United States Patent [19]
Stevens et al.

[11] Patent Number: 6,063,928
[45] Date of Patent: May 16, 2000

[54] 5-LIPOXYGENASE INHIBITORS

[75] Inventors: Rodney W. Stevens, Handa; Takashi Mano, Seishiro-cho; Kazunari Nakao, Shinbayashi-cho; Yoshiyuki Okumura, Chita, all of Japan

[73] Assignee: Pfizer Inc, New York, N.Y.

[21] Appl. No.: 09/207,342

[22] Filed: Dec. 8, 1998

Related U.S. Application Data

[62] Division of application No. 09/020,014, Feb. 6, 1998, Pat. No. 5,883,106, which is a continuation of application No. 08/809,901, filed as application No. PCT/IB95/00408, Jun. 13, 1997, which is a continuation of application No. PCT/JP94/01747, Oct. 18, 1994.

[30] Foreign Application Priority Data

Oct. 18, 1994 [WO] WIPO ................. PCT/JP94/01747

[51] Int. Cl.$^7$ ............... C07D 207/323; C07D 207/36; C07D 233/60; C07D 233/61; C07D 401/10; C07D 403/10; C07D 405/10; C07D 235/10; C07D 235/14

[52] U.S. Cl. ................... 546/269.7; 546/271.1; 546/271.4; 546/272.1; 546/272.4; 546/273.4; 546/274.4; 546/275.1; 546/275.4; 546/276.1; 546/277.4; 546/277.7; 548/146; 548/186; 548/206; 548/214; 548/255; 548/262.2; 548/265.8; 548/266.2; 548/266.8; 548/267.2; 548/267.8; 548/268.2; 548/304.7; 548/335.1; 548/373.1; 548/375.1; 548/376.1; 548/377.1; 548/361.1; 548/362.5; 548/469; 548/518; 548/523; 548/527; 549/59; 549/61; 549/62; 549/65; 549/74; 549/75; 549/472; 549/474; 549/475; 549/491; 549/497; 549/504

[58] Field of Search .............. 548/304.7, 306.1, 548/346.1, 361.1, 364.1, 365.1, 469, 511, 517, 523, 146, 215, 262.2, 255, 335.1, 373.1, 518; 546/269.7; 549/59, 472

[56] References Cited

FOREIGN PATENT DOCUMENTS

| | | |
|---|---|---|
| 462830 | 12/1991 | European Pat. Off. . |
| 488602 | 6/1992 | European Pat. Off. . |
| 505122 | 9/1992 | European Pat. Off. . |
| 540165 | 5/1993 | European Pat. Off. . |
| 9429299 | 12/1994 | WIPO . |

*Primary Examiner*—Johann Richter
*Assistant Examiner*—Jane C. Oswecki
*Attorney, Agent, or Firm*—Peter C. Richardson; Paul H. Ginsburg; Raymond M. Speer

[57] ABSTRACT

Novel compounds having the ability to inhibit 5-lipoxygenase enzyme and having the following formula I:

$$Ar^1—X^1—Ar^2—X^2—Ar^3—\underset{R^2}{\overset{Y}{\underset{|}{\overset{|}{C}}}}—R^1 \qquad I$$

and the pharmaceutically acceptable salts thereof, wherein $Ar^1$ is a heterocyclic moiety which is selected from imidazolyl, pyrrolyl, pyrazolyl, 1,2,3-triazolyl, 1,2,4-triazolyl, indolyl, indazolyl and benzimidazolyl, which is bonded to $X^1$ through a ring nitrogen atom, and which may be optionally substituted with one or two substituents selected from halo, hydroxy, cyano, amino, $C_{1-4}$ alkyl and the like; $X^1$ is a direct bond or $C_{1-4}$ alkylene; $Ar^2$ is phenylene optionally substituted with halo, hydroxy, cyano, amino and the like; $X^2$ is —A—X— or —X—A— wherein A is a direct bond or $C_{1-4}$ alkylene and X is oxy, thio, sulfinyl or sulfonyl; $Ar^3$ is phenylene, pyridylene, thienylene, furylene, oxazolylene or thiazolylene optionally substituted with one or two substituents selected from halo, hydroxy, cyano, amino, $C_{1-4}$ alkyl and the like; $R^1$ and $R^2$ are each $C_{1-4}$ alkyl, or together they form a group of formula —$D^1$—Z—$D^2$— which together with the carbon atom to which it is attached defines a ring having 3 to 8 atoms, wherein $D^1$ and $D^2$ are $C_{1-4}$ alkylene and Z is a direct bond or oxy, thio, sulfinyl, sulfonyl, or vinylene, and $D^1$ and $D^2$ may be substituted by $C_{1-3}$ alkyl; and Y is $CONR^3R^4$, CN, $C(R^3)$=N—$OR^4$, $COOR^3$, $COR^3$ or $CSNR^3R^4$, wherein $R^3$ and $R^4$ are each H or $C_{1-4}$ alkyl. These compounds are useful in the treatment or alleviation of inflammatory diseases, allergy and cardiovascular diseases in mammals and as the active ingredient in pharmaceutical compositions for treating such conditions.

4 Claims, No Drawings

5-LIPOXYGENASE INHIBITORS

The present application is a divisional of U.S. patent application Ser. No. 09/020,014, now U.S. Pat. No. 5,883,106 which was a continuation of U.S. patent application Ser. No. 08/809,901, which was a 371 application of International Patent Application PCT/IB95/00408 (which published as WO 96/11911), which was a continuation of Priority Application PCT/JP94/01747, filed Oct. 18, 1994.

TECHNICAL FIELD

This invention relates to novel compounds. The compounds of the present invention inhibit the action of lipoxygenase enzyme and are useful in the treatment or alleviation of inflammatory diseases, allergy and cardiovascular diseases in mammals. This invention also relates to pharmaceutical compositions comprising such compounds.

BACKGROUND ART

Arachidonic acid is known to be the biological precursor of several groups of biologically active endogenous metabolites. The first step in the metabolism of arachidonic acid is its release from membrane phospholipids, via the action of phospholipase A2. Arachidonic acid is then metabolized either by cyclooxygenase to produce prostaglandins including prostacyclin, and thromboxanes or by lipoxygenase to generate hydroperoxy fatty acids which may be further converted to the leukotrienes.

The leukotrienes are extremely potent substances which elicit a wide variety of biological effects, often in the nanomolar to picomolar concentration range. The peptidoleukotrienes ($LTC_4$, $LTD_4$, $LTE_4$) are important bronchoconstrictors and vasoconstrictors, and also cause plasma extravasation by increasing capillary permeability. $LTB_4$ is a potent chemotactic agent, enhancing the influx of leukocytes and inducing their subsequent degranulation at the site of inflammation. A pathophysiological role for leukotrienes has been implicated in a number of human disease states including asthma and related obstructive airway diseases, allergic rhinitis, rheumatoid arthritis and gout, psoriasis and atopic dermatitis, adult respiratory distress syndrome (ARDS), inflammatory bowel diseases (e.g. Crohn's disease), endotoxin shock, atherosclerosis and cardiovascular disorders (e.g. ischemia-induced myocardial injury) and glomerular nephritis. Any agent that inhibits the action of lipoxygenases is expected to be of considerable therapeutic value for the treatment of acute and chronic inflammatory conditions.

For a review article on lipoxygenase inhibitors, see H. Masamune and L. S. Melvin, Sr.: Annual Reports in Medicinal Chemistry, 1989, 24, pp 71–80 (Academic). More recently, further examples of lipoxygenase inhibitors have been disclosed in EP 0 462 830 A2, EP 0 505 122 A1 and EP 0 540 165 A1.

BRIEF DESCLOSURE OF THE INVENTION

The present invention provides novel chemical compounds of the following formula I

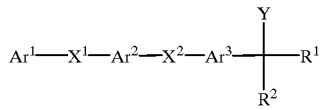

and the pharmaceutically acceptable salts thereof, wherein
$Ar^1$ is a heterocyclic moiety which is selected from the group consisting of imidazolyl, pyrrolyl, pyrazolyl, 1,2,3-triazolyl, 1,2,4-triazolyl, indolyl, indazolyl, benzimidazolyl, which is bonded to $X^1$ through a ring nitrogen atom, and which may be optionally substituted with one or two substituents selected from halo, hydroxy, cyano, amino, $C_{1-4}$ alkyl, $C_{1-4}$ alkoxy, $C_{1-4}$ alkylthio, $C_{1-4}$ halo-substituted alkyl, $C_{1-4}$ halo-substituted alkoxy, $C_{1-4}$ alkylamino and di($C_{1-4}$) alkylamino;

$X^1$ is a direct bond or $C_{1-4}$ alkylene;

$Ar^2$ is phenylene optionally substituted with one or two substituents selected from halo, hydroxy, cyano, amino, $C_{1-4}$ alkyl, $C_{1-4}$ alkoxy, $C_{1-4}$ alkylthio, $C_{1-4}$ halo-substituted alkyl and $C_{1-4}$ halo-substituted alkoxy;

$X^2$ is —A—X— or —X—A— wherein A is a direct bond or $C_{1-4}$ alkylene and X is oxy, thio, sulfinyl or sulfonyl;

$Ar^3$ is phenylene, pyridylene, thienylene, furylene, oxazolylene or thiazolylene optionally substituted with one or two substituents selected from halo, hydroxy, cyano, amino, $C_{1-4}$ alkyl, $C_{1-4}$ alkoxy, $C_{1-4}$ alkylthio, $C_{1-4}$ halo-substituted alkyl, $C_{1-4}$ halo-substituted alkoxy, $C_{1-4}$ alkylamino and di($C_{1-4}$) alkylamino;

$R^1$ and $R^2$ are each $C_{1-4}$ alkyl, or together they form a group of formula —$D^1$—Z—$D^2$— which together with the carbon atom to which it is attached defines a ring having 3 to 8 atoms, wherein $D^1$ and $D^2$ are $C_{1-4}$ alkylene and Z is a direct bond or oxy, thio, sulfinyl, sulfonyl, or vinylene, and $D^1$ and $D^2$ may be substituted by $C_{1-3}$ alkyl; and Y is $CONR^3R^4$, CN, $C(R^3)$=N—$OR^4$, $COOR^3$, $COR^3$ or $CSNR^3R^4$, wherein $R^3$ and $R^4$ are each H or $C_{1-4}$ alkyl.

The preferred meaning for $C_{1-4}$ halo-substituted alkyl is trifluoromethyl, and the preferred meaning for $C_{1-4}$ halo-substituted alkoxy is trifluoromethoxy.

A preferred group of compounds of this invention consists of compounds of the formula I, wherein $Ar^2$ is 1,4-phenylene and $Ar^3$ is 1,3-phenylene or 5-fluoro-1,3-phenylene. Within this preferred group, particularly preferred compounds are:

(1) those compounds in which $Ar^1$ is 2-alkylimidazolyl; $X^1$ is a direct bond; and Y is $CONH_2$; and (2) those compounds in which $Ar^1$ is pyrrolyl; $X^1$ is $CH_2$; and Y is $CONH_2$.

These compounds are useful in the treatment or alleviation of inflammatory diseases, allergy and cardiovascular diseases in mammals and as the active ingredient in pharmaceutical compositions for treating such conditions.

Preferrred individual compounds of this invention are the following:

4-[5-fluoro-3-[4-(2-methylimidazol-1-yl)benzyloxy]phenyl]-3,4,5,6-tetrahydro-2H-pyran-4-carboxamide;

4-[3-[4-(2-methylimidazol-1-yl)phenylthio]phenyl]-3,4,5,6-tetrahydro-2H-pyran-4-carboxamide;

4-[3-[4-(pyrrol-1-ylmethyl)phenylthio]phenyl]-3,4,5,6-tetrahydro-2H-pyran-4-carboxamide;

(2SR, 4RS)-2-methyl-4-[3-[4-(2-methylimidazol-1-yl)phenylthio]phenyl]-3,4,5,6-tetrahydro-2H-pyran-4-carboxamide; and 4-methoxyiminomethyl-4-[3-[4-(2-methylimidazol-1-yl)phenylthio]phenyl]-3,4,5,6-tetrahydro-2H-pyran.

DETAILED DESCRIPTION OF THE INVENTION

A compound of formula I, or a pharmaceutically acceptable salt thereof, may be prepared by a variety of procedures. For example, a compound of the formula I is prepared according to the reactions outlined in Scheme 1. Unless otherwise indicated, $Ar^1$, $X^1$, $Ar^2$, $X^2$, $Ar^3$, $R^1$, $R^2$ and Y in the reaction schemes and discussion that follow are defined above.

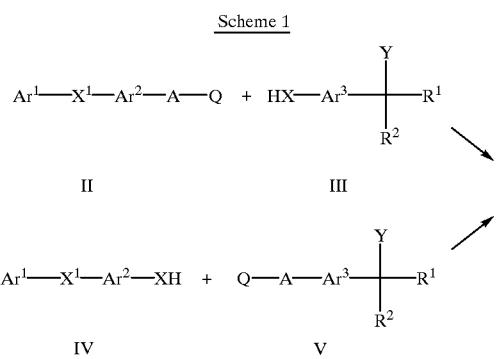

Scheme 1

In one embodiment, as outlined in Scheme 1, a compound of formula II (or formula V) wherein Q is a displaceable group is coupled with a compound of formula III (or formula IV), preferably in the presence of a suitable base. A suitable displaceable group Q is, for example, a halo or sulfonyloxy group, for example, fluoro, chloro, bromo, iodo, trifluoromethanesulfonyloxy, methanesulfonyloxy or p-toluenesulfonyloxy group, all readily accessible by conventional methods. Preferred base for the coupling reaction is, for example, an alkali or alkaline earth metal hydroxide, alkoxide, carbonate or hydride such as sodium hydroxide, potassium hydroxide, sodium methoxide, sodium ethoxide, potassium tert-butoxide, sodium carbonate, potassium carbonate, sodium hydride or potassium hydride, or an amine such as triethylamine, diisopropylethylamine or dimethylaminopyridine. Preferred reaction-inert solvents include, for example, acetone, acetonitrile, dichloromethane, N,N-dimethylacetamide, N,N-dimethylformamide, dimethylsulfoxide, dioxane or tetrahydrofuran. Reaction temperatures are preferably in the range of room temperature to reflux temperature of solvent, but if necessary, lower or higher temperature can be employed. Reaction time is in general from a few hours to several days. Conveniently the reaction may be conducted in the presence of a suitable catalyst, for example, tetrakis (triphenylphosphine)—palladium, bis(triphenylphosphine) palladium(II) chloride, cuprous oxide, cuprous iodide, cuprous bromide or cuprous chloride.

Alternatively, a compound of formula II (or formula V) wherein Q is a hydroxyl group and A is $C_1$–$C_4$ alkylene, for example methylene, is coupled with a compound of formula III (or formula IV) under Mitsunobu-type reaction conditions. Suitable condensing reagents are, for example, diethyl azodicarboxylate and triphenylphosphine and preferred reaction-inert solvents include dichloromethane, tetrahydrofuran and toluene. Reaction temperatures are preferably in the range of 0° C. through to room temperature, but if necessary, lower or higher temperature can be employed. Reaction time is in general from several minutes to several hours.

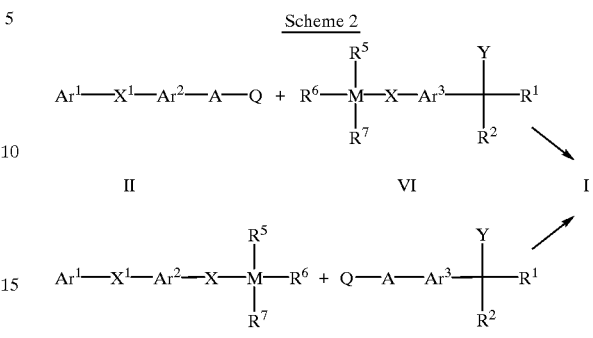

Scheme 2

In another embodiment (Scheme 2), a compound of formula II (or formula V) wherein Q is a displaceable group is coupled with a compound of formula VI (or formula VII) wherein $R^5$, $R^6$ and $R^7$ are independently a suitable alkyl such as $C_{1-4}$ alkyl or aryl such as phenyl group and M is silicon or tin (IV), preferably silicon, preferably in the presence of a suitable base. A suitable displaceable group Q is, for example, a halo or sulfonyloxy group, for example, fluoro, chloro, bromo, iodo, trifluoromethanesulfonyloxy, methanesulfonyloxy or p-toluenesulfonyloxy group, all readily accessible by conventional methods. A suitable —$MR^5R^6R^7$ group is, for example, trimethylsilyl, triisopropylsilyl, tert-butyldimethylsilyl or tert-butyldiphenylsilyl group, preferably triisopropylsilyl, or tributylstannyl, all readily accessible by conventional methods. Preferred base for the coupling reaction is, for example, an alkali or alkaline earth metal alkoxide or halide such as sodium ethoxide, sodium tert-butoxide, potassium tert-butoxide, sodium fluoride, potassium fluoride or cesium fluoride, or a quaternary ammonium salt such as tertabutylammonium fluoride. Preferred reaction-inert solvents include, for example, ethanol, acetonitrile, toluene, N,N-dimethylacetamide, N-methyl-2-pyrrolidone, N,N-dimethylformamide, dimethylsulfoxide, dioxane or tetrahydrofuran. Reaction temperatures are preferably in the range of room temperature to reflux temperature of solvent, but if necessary, lower or higher temperature can be employed. Reaction time is in general from a few minutes to several days. Conveniently the reaction may be conducted in the presence of a suitable catalyst, for example, tetrakis (triphenylphosphine)palladium, bis(triphenylphosphine) palladium (II) chloride, or the like (for example, see Tetrahedron Lett., 1994, 3225–3226).

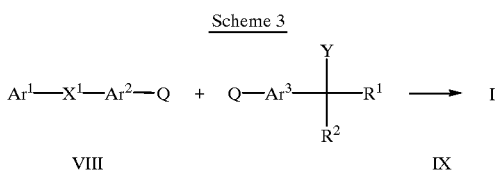

Scheme 3

Alternatively, in another embodiment, a compound of formula I wherein X is thio may be prepared as outlined in Scheme 3. Thus, a compound of formula VIII is coupled with a compound of formula IX wherein Q is a displaceable group in the presence of thiourea and a suitable catalyst, for example, tetrakis(triphenylphosphine)—palladium, or a nickel (0) catalyst generated in situ from, for example, bis(triethylphosphine)nickel(II) chloride and a suitable reducing agent such as, for example, sodium cyanoborohydride, or the like (Chem. Lett. 1986, 1379–1380). A suitable displaceable group Q is, for example, a halo or sulfonyloxy group, for example, fluoro, chloro, bromo, iodo, trifluoromethanesulfonyloxy, methanesulfonyloxy or p-toluenesulfonyloxy group, all readily accessible by conventional methods. Preferred reaction-inert solvents include, for example, ethanol, acetonitrile, toluene, N,N-dimethylacetamide, N-methyl-2-pyrrolidone, N,N-dimethylformamide, dimethylsulfoxide, dioxane or tetrahydrofuran. Reaction temperatures are preferably in the range of room temperature to reflux temperature of solvent, but if necessary, lower or higher temperature can be employed. Reaction time is in general from a few minutes to several days.

For the preparation of those compounds in Formula I wherein X is sulfinyl or sulfonyl group, a compound of formula I wherein X is thio may be oxidized by conventional methods. A suitable oxidizing agent is, for example, hydrogen peroxide, a peracid such as m-chloroperoxybenzoic or peroxyacetic acid, an alkaline metal peroxysulfate such as potassium peroxymonosulfate or the like. Preferred reaction-inert solvents include, for example, acetone, dichloromethane, chloroform, tetrahydrofuran or water. Reaction temperatures are preferably in the range 0° C. to room temperature, but if necessary, lower or higher temperature can be employed. Reaction time is in general from a few minutes to several hours.

The starting materials of the formulae II, III, IV, V, VI, VII, VIII and IX may be conveniently obtained by conventional procedures known to those skilled in the art. The preparation of such starting materials is described within the accompanying non-limiting examples which are provided for the purpose of illustration only. Alternatively, requisite starting materials may be obtained by analogous procedures, or modifications thereof, to those described hereinafter.

The products which are addressed in the aforementioned general syntheses and illustrated in the experimental examples herein may be isolated by standard methods and purification can be achieved by conventional means known to those skilled in the art, such as distillation, recrystallization and chromatography techniques.

The compounds of the present invention which contain one or more asymmetric centers are capable of existing in various stereoisomeric forms. All such individual forms, and mixtures thereof, are included within the scope of the invention. The various isomers can be obtained by standard methods. For example, racemic mixtures can be separated into the individual enantiomers by standard resolution techniques. Individual diastereomers can be obtained by stereoselective synthesis, or by separation of mixtures by fractional crystallization or chromatography techniques.

A majority of the compounds of the present invention are capable of forming addition salts with inorganic and organic acids. The pharmaceutically acceptable acid salts of the novel compounds of the present invention are readily prepared by contacting said compound with a chosen mineral or organic acid in an aqueous solvent medium, in a suitable organic solvent, such as, for example, methanol, ethanol, acetone or diethyl ether, or mixture thereof. The desired solid salt may then be obtained by precipitation or by careful evaporation of solvent.

The acids which are used to prepare the pharmaceutically acceptable acid addition salts of the aforementioned compounds of the present invention are those which form non-toxic addition salts, such as the hydrochloride, hydrobromide, hydroiodide, nitrate, sulfate or acetate, fumarate, tartrate, succinate, maleate, gluconate, saccharate, benzoate, methanesulfonate, benzenesulfonate, p-toluenesulfonate and pamoate (i.e., 1,1'-methylene-bis-(2-hydroxy-3-naphthoate)) salts.

The compounds of the invention which have also acidic groups are capable of forming base salts with various pharmaceutically acceptable cations. Examples of such salts include the alkali metal or alkaline earth metal salts and particularly, the sodium and potassium salts. These salts are all prepared by conventional techniques. The chemical bases which are used as reagents to prepare the pharmaceutically acceptable base salts of this invention are those which form non-toxic base salts. These particular non-toxic base salts include those derived from such pharmaceutically acceptable cations as sodium, potassium, calcium and magnesium, etc. These salts can easily be prepared by treating the aforementioned compounds with an aqueous solution containing the desired pharmaceutically acceptable cation, and then evaporating the resulting solution to dryness, preferably under reduced pressure. Alternatively, they may also be prepared by mixing lower alkanoic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum production of yields of the desired final product.

The compounds of the present invention inhibit the activity of 5-lipoxygenase enzyme. This inhibition can be demonstrated in vitro in assays using rat peritoneal cavity (RPC) resident cells (*Japanese Journal of Inflammation*: 1987, 7, 145–150) and heparinised human whole blood (HWB) (*Br. J. of Pharmacol.*: 1990, 99, 113–118) both of which determine the effect of said compounds on the metabolism of arachidonic acid. All of the following examples tested in the aforementioned assays were shown to possess the efficacy of inhibiting lipoxygenase activity. Some preferred compounds indicated low $IC_{50}$ values, in the range of 0.01 to 1 $\mu$M, with respect to lipoxygenase activity.

The ability of the compounds of the present invention to inhibit lipoxygenase enzyme makes them useful for controlling the symptoms induced by the endogenous metabolites arising from arachidonic acid in a mammalian subject, especially a human subject. The compounds are therefore valuable in the prevention and treatment of such disease states in which the accumulation of arachidonic acid metabolites are the causative factor; e.g. allergic bronchial asthma, skin disorders, rheumatoid arthritis and osteoarthritis.

In particular, the compounds of the present invention and their pharmaceutically acceptable salts are of use in the treatment or alleviation of inflammatory diseases in a human subject.

For treatment of the various conditions described above, the compounds and their pharmaceutically acceptable salts can be administered to a human subject either alone, or preferably in combination with pharmaceutically acceptable carriers or diluents in a pharmaceutical composition according to standard pharmaceutical practice. The compounds can be administered orally or parenterally in conventional fashion.

When the compounds are administered to a human subject for the prevention or treatment of an inflammatory disease, the oral dose range will be from about 0.1 to 10 mg/kg per body weight of the subject to be treated per day, preferably from about 0.1 to 4 mg/kg per day in single or divided doses. If parenteral administration is desired, then an effective dose will be from about 0.05 to 5 mg/kg per body weight of the subject to be treated per day. In some instances it may be necessary to use dosages outside these limits, since the dosages will necessarily vary according to the age, weight and response of the individual patient as well as the severity of the patient's symptoms and the potency of the particular compound being administered.

For oral administration, the compounds of the invention and their pharmaceutically acceptable salts can be administered, for example, in the form of tablets, powders, lozenges, syrups or capsules or as an aqueous solution or suspension. In the case of tablets for oral use, carriers which are commonly used include lactose and corn starch. Further lubricating agents such as magnesium stearate are commonly added. In the case of capsules, useful diluents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, sterile solutions of the active ingredient are usually prepared and the pH of the solutions should be suitably adjusted and buffered. For intravenous use, the total concentration of solute should be controlled to make the preparation isotonic.

In addition, particularly for the treatment of asthma, the compounds of formula I of this invention can be administered to a human subject by inhalation. For this purpose they are administered as a spray or mist, according to standard practice.

EXAMPLES

The present invention is illustrated by the following examples. However, it should be understood that the invention is not limited to the specific details of these examples. Proton nuclear magnetic resonance spectra (NMR) were measured at 270 MHz unless otherwise indicated and peak positions are expressed in parts per million (ppm) downfield from tetramethylsilane. The peak shapes are denoted as follows: s—singlet, d—doublet, t—triplet, m—multiplet and br—broad.

Example 1

1-[3-Fluoro-5-[4-(2-methylimidazol-1-yl)benzyloxy]phenyl]cyclopentane-1-carboxamide A. Ethyl 1-(3-benzyloxy-5-fluorophenyl)cyclopentane-1-carboxylate The titled compound was prepared from ethyl 3-benzyloxy-5-fluorophenylacetate according to the preparation of ethyl 4-(3-benzyloxy-5-fluorophenyl)-3,4,5,6-tetrahydro-2H-pyran-4-carboxylate except substituting 1,4-dibromobutane for bis-(2-chloroethyl) ether.

$^1$H NMR (CDCl$_3$) δ: 7.49–7.28 (5 H, m), 6.81–6.75 (1 H, m), 6.69 (1 H, ddd, J=9.9, 2.2, 2.2 Hz), 6.56 (1 H, ddd, J=10, 2.2, 2.2 Hz), 5.02 (2 H, s), 4.07 (2 H, q, J=7.0 Hz), 2.67–2.52 (2 H, m), 1.93–1.60 (6 H, m), 1.16 (3 H, t, J=7.0 Hz).

B. Ethyl 1-(5-fluoro-3-hydroxyphenyl)cyclopentane-1-carboxylate

The titled compound was prepared from ethyl 1-(3-benzyloxy-5-fluorophenyl)-cyclopentane-1-carboxylate according to the preparation of ethyl 4-(5-fluoro-3-hydroxyphenyl)-3,4,5,6-tetrahydro-2H-pyran-4-carboxylate.

$^1$H NMR (CDCl$_3$) δ: 6.68–6.58 (2 H, m), 6.48 (1 H, ddd, J=10, 2.2, 2.2 Hz), 4.12 (2 H, q, J=7.0 Hz), 2.47–2.31 (2 H, m), 1.73–1.33 (6 H, m), 1.19 (3 H, t, J=7.0 Hz).

C. Ethyl 1-[5-fluoro-3-[4-(2-methylimidazol-1-yl)benzyloxy]phenyl]cyclopentane-1-carboxylate (Claimed Compound)

The titled compound was prepared from ethyl 1-(5-fluoro-3-hydroxyphenyl)-cyclopentane-1-carboxylate according to the preparation of ethyl 4-[5-fluoro-3-[4-(2-methylimidazol-1-yl)benzyloxy]phenyl]-3,4,5,6-tetrahydro-2H-pyran-4-carboxylate (Example 2).

$^1$H NMR (CDCl$_3$) δ: 7.55 (2 H, d, J=8.4 Hz), 7.33 (2 H, d, J=8.4 Hz), 7.04 (1 H, d, J=1.5 Hz), 7.01 (1 H, d, J=1.5 Hz), 6.80–6.78 (1 H, m), 6.73 (1 H, ddd, J=9.5, 2.2, 2.2 Hz), 6.58 (1 H, ddd, J=10, 2.2, 2.2 Hz), 5.08 (2 H, s), 4.09 (2 H, q, J=7.0 Hz), 2.64–2.55 (2 H, m), 2.38 (3 H, s), 1.93–1.68 (6 H, m), 1.17 (3 H, t, J=7.0 Hz).

D. 1-[5-Fluoro-3-[4-(2-methylimidazol-1-yl)benzyloxy]phenyl]cyclopentane-1-carboxamide The desired compound was prepared from ethyl 1-[3-fluoro-5-[4-(2-methylimidazol-1-yl)benzyloxy]phenyl]cyclopentane-1-carboxylate according to the preparation of 4-[5-fluoro-3-[4-(2-methylimidazol-1-yl)benzyloxy]phenyl]-3,4,5,6-tetrahydro-2H-pyran-4-carboxamide (Example 5).

$^1$H NMR (CDCl$_3$) δ: 7.56 (2 H, d, J=8.1 Hz), 7.34 (2 H, d, J=8.1 Hz), 7.04 (1 H, s), 7.02 (1 H, s), 6.93 (1 H, dd, J=2.2, 2.2 Hz), 6.78 (1 H, ddd, J=2.2, 2.2, 9.5 Hz), 6.65 (1 H, ddd, J=2.2, 2.2, 9.5 Hz), 6.11 (2H, br. s), 5.12 (2 H, s), 2.52–2.40 (2 H, m), 2.38 (3 H, s), 2.13–1.82 (6 H, m).

Example 2

Ethyl 4-[5-fluoro-3-[4-(2-methylimidazol-1-yl)benzyloxy]phenyl]-3,4,5,6-tetra-hydro-2H-pyran-4-carboxylate A. Ethyl 4-(2-methylimidazol-1-yl)benzoate A mixture of 2-methylimidazole (50 g, 0.6 mol), ethyl 4-fluorobenzoate (100 g, 0.6 mol) and potassium carbonate (415 g, 3 mol) in dry DMSO (1.5 l) was heated at 120° C. for 66 hours under a nitrogen atmosphere. After cooling to room temperature, the reaction mixture was poured into ice-cold water (1 l), and extracted with Et$_2$O (750 ml×2). The organic phase was washed with water (500 ml) and brine (500 ml), dried over MgSO$_4$ and evaporated. The residual solid was recrystallized from ethyl acetate-hexane to give the titled compound (47 g, 33%) as yellow needles.

$^1$H NMR (CDCl$_3$) δ: 8.22–8.12 (m, 2H), 7.43–7.33 (m, 2H), 7.10–6.99 (m, 2H), 4.42 (q, J=7.0 Hz, 2H), 1.43 (t, J=7.0 Hz, 3H).

B. 4-(2-Methylimidazol-1-yl)benzyl alcohol

To a solution of ethyl 4-(2-methylimidazol-1-yl)benzoate (46 g, 0.2 mol) in dry CH$_2$Cl$_2$ (1 l) cooled to −75° C. under a nitrogen atmosphere was added diisobutyl-aluminum hydride (540 ml, 0.93 M in hexane) carefully over 30 minutes and then the mixture was allowed to warm slowly to ambient temperature. After stirring for 5 hours the reaction mixture was cooled in an ice-bath and methanol (30 ml) carefully added. A 30% aqueous solution of Rochelle's salt (500 ml) was then added and the mixture stirred at ambient temperature for 16 hours. Insolubles (essentially product) were removed by filtration and the organic phase separated and washed with water (500 ml), dried (MgSO$_4$) and evaporated. The combined resultant solids were recrystallized from ethanol (ca 300 ml) to afford the titled compound (35.6 g, 95%) as white needles.

$^1$H NMR (DMSO-d$_6$) δ: 7.50–7.33 (4 H, m), 7.25 (1 H, d, J=1.1 Hz), 6.90 (1 H, d, J=1.1 Hz), 5.33 (1 H, t, J=6.0 Hz), 4.56 (2 H, d, J=6.0 Hz), 2.27 (3 H, s).

C. 4-(2-Methylimidazol-1-yl)benzyl chloride hydrochloride 4-(2-Methylimidazol-1-yl)benzyl alcohol (1.28 g, 6.8 mmol) in $SOCl_2$ (5 ml) was stirred at ambient temperature for 30 minutes and then volatiles removed under reduced pressure. The resultant crude product was washed with minimal dry $Et_2O$ and dried in vacuo to afford the titled compound (1.65 g, quant.) as white solids.

$^1$H NMR (DMSO-$d_6$) δ: 7.91 (1 H, d, J=1.84 Hz), 7.79 (1 H, d, J=1.84 Hz), 7.72 (2 H, d, J=8.80 Hz), 7.66 (2 H, d, J=8.80 Hz), 4.89 (2 H, s), 2.56 (3 H, s).

D. Diethyl 3-benzyloxy-5-fluorophenylmalonate

To a stirred solution of diethyl malonate (110.2 g, 688 mmol) in dioxane(1 l) at 0° C. under a nitrogen atmosphere was added sodium hydride (27.5 g, 688 mmol, 60% dispersion in mineral oil) in portions. After stirring at 0° C. for 20 min and at room temperature for 80 min, cuprous bromide (98.7 g, 688 mmol) and a solution of 3-benzyloxy-5-fluorophenylbromide (J. Med, Chem., 1992, 35, 2600.) (96.7 g, 344 mmol) in dioxane (100 ml) were added, and the resulting suspension was heated at reflux with stirring for 4.5 hr. The reaction was quenched by adding 6N hydrogen chloride (120 ml) at 0° C., diluted with water (1 l) and extracted with n-hexane (3×700 ml). The combined extracts were washed with water (2×500 ml), saturated sodium bicarbonate (500 ml), water (500 ml) and brine (500 ml), dried (magnesium sulfate) and concentrated under reduced pressure to give 147.5 g of crude product as an amber liquid. Purification was performed by column chromatography (silica-gel, 1.7 kg; ethyl acetate in n-hexane, increasing the ratio of ethyl acetate from 5% to 20%) to give 60.8 g of a mixture of the title compound and diethyl malonate in the ratio of 1:1 as a colorless liquid. Yield of the titled compound was 34%.

$^1$H NMR (CDCl$_3$) δ: 7.46–7.31 (5 H, M), 6.85–6.81 (1 H, M), 6.76 (1 H, ddd, J=1.82, 2.20, 9.16 Hz), 6.66 (1 H, ddd, J=2.20, 2.56, 10.62 Hz), 5.04 (2 H, s), 4.54 (1 H, s), 4.30–4.16 (4 H, m), 1.32–1.22 (6 H, m).

E. Ethyl 3-benzyloxy-5-fluorophenylacetate

The above mixture of a mixture of diethyl 3-benzyloxy-5-fluorophenylmalonate and diethyl malonate (ca. 1:1.2, 1.0 g), DMSO (10 ml), water (0.1 ml), and LiCl (346 mg) were placed in a 50 ml round-bottom flask equipped with a magnetic stirrer and fitted with a condenser. The mixture was heated at reflux for 5 hr. The mixture was poured into water (50 ml) and the whole extracted with n-hexane (2×50 ml). The combined organic extracts were washed with water (50 ml), brine (50 ml) and dried over $Na_2SO_4$. Removal of solvent gave 283 mg (57%) of ethyl 3-benzyloxy-5-fluorophenylacetate as a yellow oil.

$^1$H NMR (CDCl$_3$) δ: 7.50–7.30 (5 H, m), 6.77–6.50 (3 H, m), 5.02 (2 H, s), 4.16 (2 H, q, J=7.3 Hz), 3.56 (2 H, s), 1.26 (3 H, t, J=7.3 Hz)

F. Ethyl 4-[3-(benzyloxy)-5-fluorophenyl]-3,4,5,6-tetrahydro-2H-pyran-4-carboxylate To a stirred solution of ethyl 3-(benzyloxy)-5-fluorophenylacetate (17.5 g, 61 mmol) and 15-crown-5 (1.32 g, 6 mmol) in DMF (300 ml) at room temperature was added sodium hydride (5.37 g, 134 mmol, 60% dispersion in mineral oil) in portions. After stirring at room temperature for 25 min, sodium iodide (1.32 g, 6 mmol) and bis(2-chloroethyl)ether (9.14 g, 61 mmol) were added. After 1 day the mixture was diluted with 0.5 N hydrogen chloride (500 ml) and extracted with ether (3×500 ml). The combined extracts were washed with water (500 ml), saturated sodium bicarbonate (500 ml), water (500 ml) and brine (500 ml), dried (magnesium sulfate) and concentrated under reduced pressure to give 26.15 g of crude product as a yellow liquid.

Column chromatography (silica-gel, 1 kg; 20% ethyl acetate in n-hexane) gave the titled compound as a colorless liquid (12.7 g, 58%).

$^1$H NMR (CDCl$_3$) δ: 7.45–7.31 (5 H, m), 6.81–6.78 (1 H, m), 6.70 (1 H, ddd, J=1.83, 2.20, 10.25 Hz), 6.59 (1 H, ddd, J=2.20, 2.20, 10.25 Hz), 5.03 (2 H, s), 4.14 (2 H, q, J=6.96 Hz), 3.92 (2 H, ddd, J=3.29, 4.03, 11.72 Hz), 3.54 (2 H, ddd, J=2.20, 11.35, 11.72 Hz), 2.50–2.40 (2 H, m), 1.92 (2 H, ddd, J=4.03, 11.35, 13.55 Hz), 1.19, (3 H, t, J=6.96 Hz).

G. Ethyl 4-(5-fluoro-3-hydroxyphenyl)-3,4,5,6-tetrahydro-2H-pyran-4-carboxylate

A mixture of ethyl 4-[3-(benzyloxy)-5-fluorophenyl]-3,4,5,6-tetrahydro-2H-pyran-4-carboxylate (2.70 g, 7.5 mmol) and 10% palladium on activated carbon (0.27 g) in ethanol (100 ml) was stirred under a hydrogen atmosphere for 3.25 hr. Catalyst was removed by filtration and evaporation of the filtrate gave the titled compound as a colorless liquid (2.01 g, quantitative yield).

$^1$H NMR (CDCl$_3$) δ: 6.72–6.62 (2 H, m), 6.47 (1 H, ddd, J=2.20, 2.20, 10.25 Hz), 5.40 (1 H, br s), 4.17 (2 H, q, J=6.96 Hz), 3.98–3.89 (2 H, m), 3.61–3.49 (2 H, m), 2.50–2.41 (2 H, m), 2.00–1.86 (2 H, m), 1.24, (3 H, t, J=6.96 Hz).

H. Ethyl 4-[5-fluoro-3-[4-(2-methylimidazol-1-yl)benzyloxy]phenyl]-3,4,5,6-tetrahydro-2H-pyran-4-carboxylate A stirred mixture of ethyl 4-(5-fluoro-3-hydroxyphenyl)-3,4,5,6-tetrahydro-2H-pyran-4-carboxylate (2.01 g, 7.5 mmol), 4-(2-methylimidazol-1-yl)benzyl chloride hydrochloride (1.82 g, 7.5 mmol) and potassium carbonate (5.18 g, 37.5 mmol) in DMF (30 ml) was heated at 100° C. for 1.33 hr. After cooling to room temperature, the mixture was diluted with a mixture of ethyl acetate and toluene (2:1, 200 ml), and washed with water (4×100 ml) and brine (100 ml), dried (magnesium sulfate) and concentrated to give 3.38 g of crude product as amber solids. Recrystallization from a mixture of isopropyl ether (25 ml) and ethyl acetate (2 ml) gave the titled compound (2.22 g, 68%).

$^1$H NMR (CDCl$_3$) δ: 7.55 (2 H, d, J=8.43 Hz), 7.34 (2 H, d, J=8.43 Hz), 7.04 (1 H, d, J=1.50 Hz), 7.01 (1 H, d, J=1.0 Hz), 6.82 (1 H, dd, J=2.20, 2.20 Hz), 6.75 (1 H, ddd, J=2.20, 2.20, 10.26 Hz), 6.62 (1 H, ddd, J=2.20, 2.20, 10.26 Hz), 5.09 (2 H, s), 4.16 (2 H, q, J=7.33 Hz), 3.98–3.88 (2 H, m), 3.60–3.50 (2 H, m), 2.51–2.42 (2 H, m), 2.38 (3 H, s), 2.01–1.86 (2 H, m), 1.21 (3 H, t, J=7.33 Hz).

Example 3

4-Acetyl-4-[5-fluoro-3-[4-(2-methylimidazol-1-yl)benzyloxy]phenyl]-3,4,5,6-tetrahydro-2H-pyran A. 4-[3-(Benzyloxy)-5-fluorophenyl]-4hydroxymethyl-3,4,5,6-tetrahydro-2H-pyran To a stirred solution of ethyl 4-[3-(benzyloxy)-5-fluorophenyl]-3,4,5,6-tetrahydro-2H-pyran-4-carboxylate (1.54 g, 4.3 mmol) in ether (150 ml) was added lithium aluminium hydride (0.16 g, 4.3 mmol) in three portions. The resulting suspension was stirred at room temperature under a nitrogen atmosphere for 20 min. Excess of hydride was destroyed by adding saturated aqueous sodium sulfate. The mixture was diluted with 10% aqueous sulfuric acid (100 ml) and the organic layer was separated. The ethereal layer was washed with water (100 ml), saturated aqueous sodium bicarbonate (100 ml) and brine (100 ml), dried (magnesium sulfate) and concentrated to dryness to afford the titled compound as white solids (1.28 g, 94%).

$^1$H NMR (CDCl$_3$) δ: 7.44–7.33 (5 H, m), 6.78–6.58 (3 H, m), 5.05 (2 H, s), 3.84–3.73 (2 H, m), 3.62–3.48 (4 H, m), 2.13–2.00 (2 H, m), 1.95–1.82 (2 H, m), 1.09 (1 H, t, J=6.96 Hz).

B. 4-[3-(Benzyloxy)-5-fluorophenyl]-4formyl-3,4,5,6-tetrahydro-2H-pyran

Tetra-n-propylammonium perruthenate (70 mg, 0.2 mmol) was added in one portion to a stirred mixture of 4-[3-(benzyloxy)-5-fluorophenyl]-4-hydroxymethyl-3,4,5,6-tetrahydro-2H-pyran (1.28 g, 4.0 mmol), N-methylmorpholine N-oxide (0.70 g, 6.0 mmol) and powdered 3 Å molecular sieves (2.0 g) at room temperature under nitrogen atmosphere. After 20 min tetra-n-propylammonium perruthenate (30 mg, 0.085 mmol) and N-methylmorpholine N-oxide (0.30 g, 2.6 mmol) were added and stirring continued for 30 min. The mixture was chromatographed (silica-gel, 110 g: 25% ethyl acetate in n-hexane) to give the titled compound as a colorless liquid (1.08 g, 86%).

$^1$H NMR (CDCl$_3$) δ: 9.38 (1 H, s), 7.44–7.32 (5 H, m), 6.70–6.58 (3 H, m), 5.03 (2 H, s), 3.89 (2 H, ddd, J=4.03, 4.03, 12.09 Hz), 3.62–3.51 (2 H, m), 2.38–2.28 (2 H, m), 2.09–1.97 (2 H, m).

C. 4-[3-(Benzyloxy)-5-fluorophenyl]-4(1-hydroxyethyl)-3,4,5,6-tetrahydro-2H-pyran To a stirred solution of 4-[3-(benzyloxy)-5-fluorophenyl]-4-formyl-3,4,5,6-tetrahydro-2H-pyran (1.08 g, 3.4 mmol) in THF (16 ml) at room temperature under a nitrogen atmosphere was added on 0.96 M solution of methyl magnesium bromide (5.3 ml, 5.1 mmol) in a dropwise manner. The mixture was stirred overnight, diluted with saturated aqueous ammonium chloride (40 ml) and extracted with dichloromethane (2×40 ml). The combined organic layers were washed with water (40 ml) and brine (40 ml), dried (magnesium sulfate) and concentrated to dryness. Purification by column chromatography (silica-gel, 150 g, ethyl acetate in n-hexane as an eluent increasing the amount of ethyl acetate from 40% to 60%) afforded the titled compound as a colorless liquid (0.71 g, 63%).

$^1$H NMR (CDCl$_3$) δ: 7.47–7.32 (5 H, m), 6.73–6.70 (1 H, m), 6.67–6.60 (2 H, m), 5.05 (2 H, s), 3.85–3.75 (2 H, m), 3.64 (1 H, dt, J=6.96, 6.96 Hz), 3.47–3.27 (2 H, m), 2.28–2.20 (1 H, m), 2.06–2.00 (1 H, m), 1.93–1.78 (2 H, m), 1.11 (1 H, d, J=6.96 Hz), 0.90 (3 H, d, J=6.96 Hz).

D. 4-(5Fluoro-3-hydroxyphenyl)-4-(1-Hydroxyethyl)-3,4,5,6-tetrahydro-2H-pyran

The titled compound was obtained according to the procedure described in Example 2G for the preparation of ethyl 4-[5-fluoro-3-hydroxyphenyl]-3,4,5,6-tetrahydro-2H-pyran-4-carboxylate using 4-(1-hydroxyethyl)-4-[3-(benzyloxy)-5-fluorophenyl]-3,4,5,6-tetrahydro-2H-pyran.

$^1$H NMR (DMSO-d$_6$) δ: 9.70 (1 H, brs), 6.60–6.52 (2 H, m), 6.40 (1 H, ddd, J=2.20, 2.20, 10.63 Hz), 4.62 (1 H, br d, J=4.76 Hz), 3.77–3.61 (2 H, m), 3.54–3.41 (1 H, m), 3.30–3.12 (2 H, m), 2.11–2.00 (1 H, m), 1.95–1.72 (3 H, m), 0.70 (3 H, d, J=6.23 Hz).

E. 4-Acetyl-4-(3-fluoro-5-hydroxyphenyl)-3,4,5,6-tetrahydro-2H-pyran

The titled compound was obtained according to the procedure described in Example 3B for the preparation of 4-[3-(benzyloxy)-5-fluorophenyl]-4-formyl-3,4,5,6-tetrahydro-2H-pyran using 4-(5-fluoro-3-hydroxyphenyl)-4-(1-hydroxyethyl)-3,4,5,6-tetrahydro-2H-pyran.

$^1$H NMR (CDCl$_3$) δ: 6.61 (1 H, d, J=1.84, 2.20, 9.90 Hz), 6.55–6.47 (2 H, m), 5.90 (1 H, br s), 3.85 (2 H, ddd, J=4.40, 4.40, 12.09 Hz), 3.59 (2 H, ddd, J=2.20, 9.42, 12.09 Hz), 2.40–2.29 (2 H, m), 2.19–2.18 (2 H, m), 1.97 (3 H, s).

F. 4-Acetyl-4-[5-fluoro-3-[4-(2-methylimidazol-1-yl)benzyloxy]phenyl]-3,4,5,6-tetrahydro-2H-pyran The titled compound was obtained according to the procedure described in Example 2H for the preparation of ethyl 4-[5-fluoro-3-[4-(2-methylimidazol-1-yl)benzyloxy]phenyl]-3,4,5,6-tetrahydro-2H-pyran-4-carboxylate using 4-(5-fluoro-3-hydroxyphenyl)-4-(1-hydroxyethyl)-3,4,5,6-tetrahydro-2H-pyran instead of ethyl 4-(5-fluoro-3-hydroxyphenyl)-3,4,5,6-tetrahydro-2H-pyran-4-carboxylate.

$^1$H NMR (CDCl$_3$) δ: 7.54 (2 H, d, J=8.43 Hz), 7.34 (2 H, d, J=8.43 Hz), 7.05 (1 H, d, J=1.47 Hz), 7.02 (1 H, d, J=1.47 Hz), 6.72–6.61 (3 H, m), 5.08 (2 H, s), 3.84 (2 H, ddd, J=4.40, 4.40, 12.09 Hz), 3.58 (2 H, ddd, J=2.57, 9.52, 12.09 Hz), 2.38 (3 H, s), 2.41–2.31 (2 H, m), 2.20 (2 H, ddd, J=4.40, 9.52, 14.29 Hz), 1.95 (3 H, s).

Example 4

4-[5-Fluoro-3-[4-(2-methylimidazol-1-yl)benzyloxy]phenyl]-3,4,5,6-tetrahydro-2H-pyran-4-carboxylic acid A stirred mixture of ethyl 4-[5-fluoro-3-[4-(2-methylimidazol-1-yl)benzyloxy]phenyl]-3,4,5,6-tetrahydro-2H-pyran-4-carboxylate (Example 2) (1.10 g, 25 mmol), an aqueous solution of lithium hydroxide (0.13 g, 30 mmol, 5 ml), methanol (15 ml) and THF (15 ml) was refluxed for 24 hr. The reaction mixture was neutralized with 1N hydrogen chloride. Volatiles were removed by evaporation under reduced pressure. The residue was suspended into a mixture of water (20 ml) and phosphate buffer (pH=7, 5 ml) and heated to reflux for 30 min. After cooling to 0° C., solids were collected by filtration, washed with water and then with ether and dried to constant weight under vacuum at 80° C. for 14 hr to afford the titled compound as white solids (0.98 g, 96%).

$^1$H NMR (DMSO-d6) δ: 7.62 (2 H, d, J=8.43 Hz), 7.48 (2 H, d, J=8.43 Hz), 7.30 (1 H, d, J=1.10 Hz), 6.92 (1 H, d, J=1.10 Hz), 6.90–6.76 (3 H, m), 5.19 (2 H, s), 3.84–3.75 (2 H, m), 3.50–3.40 (2 H, m), 2.36–2.27 (2 H, m), 2.29 (3 H, s), 1.88–1.75 (2 H, m).

Example 5

4-[5-Fluoro-3-[4-(2-methylimidazol-1-yl)benzyloxy]phenyl]-3,4,5,6-tetrahydro-2H-pyran-4-carboxamide To a stirred suspension of 4-[5-fluoro-3-[4-(2-methylimidazol-1-yl)benzyloxy]phenyl]-3,4,5,6-tetrahydro-2H-pyran-4-carboxylic acid (616 mg, 1.5 mmol) in dichloromethane (20 ml) at 0° C. under a nitrogen atmosphere was added oxalyl chloride (419 mg, 3.3 mmol). The resulting suspension was stirred at 0° C. for 30 min and then at room temperature for 1 hr. The resulting white suspension was concentrated to dryness and the residue added to a stirred aqueous ammonia solution (26%, 20 ml). After stirring at room temperature for 70 min., solids were collected by filtration, washed with water and dried to constant weight under vacuum at 80° C. overnight to give the titled compound (337 mg, 54%).

$^1$H NMR (DMSO-d$_6$) δ: 7.61 (2 H, d, J=8.43 Hz), 7.48 (2 H, d, J=8.43 Hz), 7.30 (1 H, d, J=1.08 Hz), 7.24 (1 H, br s), 7.08 (1 H, br s), 6.92 (1 H, d, J=1.08 Hz), 6.89–6.82 (2 H, m), 6.80–6.75 (1 H, m), 5.18 (2 H, s), 3.66–3.57 (2 H, m), 3.51–3.40 (2 H, m), 2.44–2.35 (2 H, m), 2.29 (3 H, s), 1.84–1.72 (2 H, m).

Example 6

N,N-Dimethyl-4-[5-fluoro-3-[4-(2-methylimidazol-1-yl)benzyloxy]phenyl]-3,4,5,6-tetrahydro-2H-pyran-4-carboxamide To a stirred suspension of 4-[5-fluoro-3-[4-(2-methylimidazol-1-yl)benzyloxy]phenyl]-3,4,5,6-tetrahydro- 2H-pyran-4-carboxylic acid (100 mg, 0.24 mmol), dimethylamine hydrochloride (98 mg, 1.2 mmol) and triethylamine (253 mg, 2.5 mmol) in THF (50 ml) at 0° C. was added diethyl cyanophosphonate (44 mg, 0.27 mmol). After 10 min, the reaction was diluted with water (50 ml) and extracted with ethyl acetate (50 ml). The extract was washed with water (50 ml) and brine (50 ml), dried over magnesium sulfate and concentrated. Purification of the residue was performed by column chromatography (silica-gel, 50 g; gradient polarity of eluant from dichloromethane to 5% methanol in dichloromethane) to give 117 mg of crude product as a colorless foam. Recrystallization from a mixture of isopropyl ether-ethyl acetate (1:1) to give the titled compound (51 mg, 50%).

$^1$H NMR (CDCl$_3$) δ: 7.54 (2 H, d, J=8.43 Hz), 7.33 (2 H, d, J=8.43 Hz), 7.04 (1 H, d, J=1.10 Hz), 7.01 (1 H, d, J=1.10 Hz), 6.69–6.58 (3 H, m), 5.08 (2 H, s), 3.93–3.85 (2 H, m), 3.83–3.72 (2 H, m), 2.67 (6 H, br s), 2.38 (3 H, s), 2.28-2.19 (2 H, m), 2.05–1.92 (2 H, m).

Example 7

4-Cyano-4-[3-[4-(2-methylimidazol-1-yl)benzloxy]phenyl]-3,4,5,6-tetrahydro-2H-pyran A. 4-Cyano-4-(3-methoxyphenyl)-3,4,5,6-tetrahydro-2H-pyran The titled compound was prepared according to the procedure described in Example 2F except that (3-methoxyphenyl)acetonitrile was used in place of ethyl 4-[3-(benzyloxy)-5-fluorophenyl]-3,4,5,6-tetrahydro-2H-pyran-4-carboxylate.

$^1$H NMR (CDCl$_3$) δ: 7.34 (1 H, dd, J=8.1, 8.1 Hz), 7.02–6.98 (2 H, m), 6.93–6.84 (1 H, m), 4.19–3.75 (4 H, m), 3.84 (3 H, s), 2.22–1.98 (4 H, m).

B. 4-Cyano-4-(3-hydoxyphenyl)-3,4,5,6-tetrahydro-2H-pyran

The titled compound was prepared according to the procedure described in Example 20B except that 4-cyano-4-(3-methoxyphenyl)-3,4,5,6-tetrahydro-2H-pyran was used in place of methyl 1-(3-fluoro-5-methoxyphenyl)cyclopent-3-ene-1-carboxylate.

$^1$H NMR (CDCl$_3$) δ: 7.36–7.21 (1 H, m), 7.10–6.95 (2 H, m), 6.89–6.77 (1 H, m), 5.79 (1 H, s), 4.21–4.03 (2 H, m), 4.00–3.80 (2 H, m), 2.25–1.95 (4 H, m).

C. 4-Cyano-4-[3-[4-(2-methylimidazol-1-yl)benzyloxy]phenyl]-3,4,5,6-tetrahydro-2H-pyran 4-Cyano-4-(3-hydroxyphenyl)-3,4,5,6-tetrahydro-2H-pyran was reacted with 4-(2-methylimidazol-1-yl)benzylchloride to give the titled compound in 38% yield as colorless needles according to the procedure described in Example 2H.

$^1$H NMR (CDCl$_3$) δ: 7.57 (2 H, d, J=8.4 Hz), 7.42–7.29 (3 H, m), 7.19–6.93 (5 H, m), 5.15 (2 H, s), 4.16–3.81 (4 H, m), 2.38 (3 H, s), 2.22–2.00 (4 H, m). IR(KBr): n 1610, 1585, 1519, 1489, 1416, 1391 cm-1. mp: 153–154° C.

Example 8

4-[3-[4-(2-Methylimidazol-1-yl)phenylthio]phenyl]-3,4,5,6-tetrahydro-2H-pyran-4-carboxamide A. 4-(2-Methylimidazol-1-yl)phenyliodide To a stirred solution of 2-methylimidazole (13.6 g, 165 mmol) in DMF (500 ml) was added sodium hydride (6.60 g, 165 mmol, 60% dispersion in mineral oil) in portions. The resulting white suspension was stirred at room temperature for 30 min, 4-fluoroiodobenzene (33.3 g, 150 mmol) added and the mixture heated at 100° C. After 16 hr, the bulk of DMF was removed by evaporation. The residue was then partitioned between a mixture of ethyl acetate-toluene (2:1, 500 ml) and water(250 ml). The organic layer was separated and washed with water (250 ml). Product was extracted with 10% aqueous hydrogen chloride (2×200 ml) and the combined aqueous extracts neutralized with 30% aqueous potassium hydroxide. The resulting suspension was extracted with a mixture of ethyl acetate-toluene (2:1, 3×250 ml) and the combined organic extracts washed with water (2×250 ml), brine (250 ml), dried (magnesium sulfate) and concentrated to dryness. The residue was recrystallized from toluene to afford the titled compound as off-white solids (21.9 g, 51%).

$^1$H NMR (CDCl$_3$) δ: 7.65–7.61 (2 H, m), 7.32–7.26 (2 H, m), 7.33 (1 H, d, J=1.47 Hz), 6.98 (1 H, d, J=1.47 Hz), 2.83 (3 H, s).

B. Ethyl 4-(3-bromophenyl)-3,4,5,6-tetrahydro-2H-pyran-4-carboxylate

To a stirred solution of ethyl 3-bromophenylacetate (Guenther, O. et al, Chem. Ber., 1967, 100, 425) (41.3 g, 170 mmol) and 15-crown-5 (3.74 g, 17 mmol) in DMF (1 L) at room temperature was added sodium hydride (14.8 g, 370 mmol, 60% dispersion in mineral oil) in portions. After stirring at room temperature for 40 min, sodium iodide (25.5 g, 170 mmol) and bis(2-chloroethyl)ether (30.4 g, 210 mmol) were added. After 10.5 hr the bulk of DMF was removed under reduced pressure. The residue was covered with a mixture of ethyl acetate and toluene (1:1, 500 ml) and washed with 0.5 N hydrogen chloride (500 ml). The aqueous layer was extracted with a mixture of ethyl acetate-toluene (1:1, 2×500 ml) and the combined extracts were washed with water (250 ml), saturated sodium bicarbonate (250 ml), water (2×250 ml) and brine (250 ml), dried (magnesium sulfate) and concentrated under reduced pressure to give 56.8 g of crude product as an orange liquid. Purification by column chromatography (silica-gel, 700 g; 15% then 20% ethyl acatate in n-hexane) gave the titled compound as a yellow liquid (36.5 g, 69%).

$^1$H NMR (CDCl$_3$) δ: 7.52 (1H, dd, J=1.83, 1.83 Hz), 7.40 (1H, ddd, J=1.83, 1.83, 7.70 Hz), 7.31 (1 H, ddd, 1.83, 1.83, 8.06 Hz), 7.22 (1 H, dd, J=7.70, 8.06 Hz), 4.16 (2 H, q, J=7.33 Hz), 3.94 (2 H, ddd, J=3.29, 4.03, 11.73 Hz), 3.56 (2 H, ddd, J=2.20, 11.73, 13.56 Hz), 2.50 (2 H, ddd, J=2.20, 3.29, 11.36 Hz), 1.94 (2 H, ddd, J=4.03, 11.36, 13.56 Hz), 1.20 (3 H, t, J=7.33 Hz).

C. 4-(3-Bromophenyl)-3,4,5,6-tetrahydro-2H-pyran-4-carboxylic acid

A stirred mixture of ethyl 4-(3-bromophenyl)-3,4,5,6-tetrahydro-2H-pyran-4-carboxylate (36.5 g, 117 mmol), an aqueous solution of lithium hydroxide (6.14 g, 146 mmol, 50 ml), methanol (150 ml) and THF (150 ml) was refluxed for 1 day. The reaction mixture was partitioned between ether (100 ml) and 10% aqueous potassium hydroxide solutuion (300 ml). The ethereal layer was separated, extracted with 10% aqueous potassium hydroxide solutuion (2×100 ml) and discarded. The combined aqueous extracts were acidified with concentrated hydrogen chloride and the resulting white precipitates were collected by filtration, washed with water and dried to constant weight under vacuum at 80° C. to give the titled compound as white solids (26.4 g, 79%).

$^1$H NMR (CDCl$_3$) δ: 7.55 (1 H, dd, J=1.83, 1.83 Hz), 7.43 (1 H, ddd, J=1.46, 1.83, 8.06 Hz), 7.35 (1 H, ddd, J=1.46, 1.83, 8.06 Hz), 7.24 (1 H, dd, J=8.06, 8.06 Hz), 3.94 (2 H, ddd, J=3.67, 4.03, 12.09 Hz), 3.62 (2 H, ddd, J=1.83, 11.72, 12.09 Hz), 2.50 (2 H, m), 1.97 (2 H, ddd, J=4.03, 11.72, 13.92 Hz).

D. Methyl4-(3-methylsulfinylphenyl)-3,4,5,6-tetrahydro-2H-pyran-4-carboxylate

To a stirred solution of 4-(3-bromophenyl)-3,4,5,6-tetrahydro-2H-pyran-4-carboxylic acid (19.1 g, 67 mmol) in THF (650 ml) at −78° C. under a nitrogen atmosphere was added a solution of n-butyllithium (1.60 M in n-hexane solution, 100 ml, 160 mmol). After 45 min a solution of dimethyl disulfide (8.84 g, 94 mmol) in THF (50 ml) was added slowly over 30 min and the mixture was stirred at −78° C. for further 70 min and then at ambient temperature for 3 hr. To the resulting suspension was added 2N hydrogen chloride (500 ml) and the layers were separated. The aqueous layer was extracted with ethyl acetate (2×250 ml) and the combined organic layers washed with water (4×100 ml) and brine (100 ml), dried (magnesium sulfate) and concentrated to dryness.

The residue (21.5 g) was dissolved in methanol (100 ml) and 10% methanolic hydrogen chloride (100 ml) was added and the mixture was heated at reflux with stirring for 13 hr. Another portion of 10% methanolic hydrogen chloride (100 ml) was added and heating was continued for another 7 hr. Volatiles were removed by evaporation and the residue was dissolved in ethyl acetate (500 ml), and washed with water (2×250 ml), saturated aqueous sodium bicarbonate (250 ml), water (250 ml) and brine (250 ml). The aqueous layers were combined and extracted with ethyl acetate (2×250 ml). The combined organic layers were dried (magnesium sulfate) and concentrated to dryness.

This product (17.9 g) was dissolved in methanol (200 ml) and cooled to 0° C. A solution of sodium periodate (16.0 g, 75 mmol) in water (200 ml) was added and the resulting suspension was stirred at 0° C. for 1 hr. The reaction mixture was diluted with water (500 ml) and extracted with dichloromethane (200 ml) and 10% methanol in dichloromethane (3×200 ml). The combined extracts were washed with brine (200 ml), dried (magnesium sulfate) and concentrated to dryness. Purification by column chromatography (silica-gel, 700 g; ethyl acetate) gave the titled compound as a colorless liquid (12.2 g, 64%), which solidified on standing.

$^1$H NMR (CDCl$_3$) δ: 7.71–7.68 (1 H, m), 7.55–7.50 (3 H, m), 4.02–3.92 (2 H, m), 3.69 (3 H, s), 3.62–3.50 (2 H, m), 2.73 (3 H, s), 2.62–2.52 (2 H, m), 2.06–1.59 (2 H, m).

E. Methyl 4-(3-mercaptophenyl)-3,4,5,6-tetrahydro-2H-pyran-4-carboxylate

Methyl 4-(3-methylsulfinylphenyl)-3,4,5,6-tetrahydro-2H-pyran-4-carboxylate (12.2 g, 43 mmol) was dissolved in trifluoroacetic anhydride (50 ml) and heated at reflux for 30 min. Volatiles were removed by evaporation and the residue was dissolved into methyl alcohol (100 ml). Triethylamine (100 ml) was added over 5 min and the mixture concentrated to dryness. The residue was dissolved in ethyl acetate (500 ml), washed with saturated aqueous ammonium chloride (200 ml) and brine (200 ml), dried (magnesium sulfate) and concentrated to dryness to provide crude titled compound as a pale black liquid which was used as such without further purification.

$^1$H NMR (CDCl$_3$) δ: 7.30–7.13 (3 H, m), 4.00–3.90 (2 H, m), 3.68 (3 H, s), 3.64–3.48 (2 H, m), 2.58–2.48 (2 H, m), 2.04–1.93 (2 H, m).

F. Ethyl 4-[3-[4-(2-methylimidazol-1-yl)phenylthio]phenyl]-3,4,5,6-tetrahydro-2H-pyran-4-carboxylate (Claimed Compound)

A solution of methyl 4-(3-mercaptophenyl)-3,4,5,6-tetrahydro-2H-pyran-4-carboxylate (1.04 g, 3.5 mmol), 4-(2-methylimidazol-1-yl)phenyliodide (0.89 g, 3.5 mmol), sodium t-butoxide (673 mg, 7 mmol) and tetrakis(triphenylphosphine)palladium (162 mg, 0.14 mmol) in dry ethanol (20 ml) was heated to reflux with stirring overnight. Volatiles were removed by evaporation and the residue was partitioned between ethyl acetate (100 ml) and water (100 ml). The aqueous layer was extracted with ethyl acetate (100 ml). The combined organic layers were washed with brine (100 ml), dried (magnesium sulfat) and concentrated to dryness to give 1.09 g of crude product as a brown liquid. Purification by column chromatography (silica-gel, 50 g; methanol in dichloromethane, increasing the ratio of methanol from 0% to 4%) afforded the titled compound (0.90 g).

$^1$H NMR (CDCl$_3$) δ: 7.51–6.98 (10 H, m), 4.15 (2 H, d, J=6.96 Hz), 3.98–3.88 (2H, m), 3.61–3.50 (3 H, m), 2.55–2.45 (2 H, m), 2.37 (3 H, s), 2.01–1.90 (2 H, m), 1.18 (3 H, t, J=6.96 Hz).

G. 4-[3-[4-(2-Methylimidazol-1-yl)phenylthio]phenyl]-3,4,5,6-tetrahydro-2H-pyran-4-carboxylic acid (Claimed Compound)

To a solution of ethyl 4-[3-[4-(2-methylimidazol-1-yl)phenylthio]phenyl]-3,4,5,6-tetrahydro-2H-pyran-4-carboxylate obtained as above in a mixture of tetrahydrofuran (20 ml) and methanol (20 ml) was added an aqueous solution of lithium hydroxide (0.42 g, 10 mmol) and the mixture heated at reflux with stirring for 11 hrs. Volatiles were then removed under reduced pressure. The residue was partitioned between ether (100 ml) and water (100 ml) and the ethereal layer was extracted with 1N aqueous potassium hydroxide (2×50 ml). The combined aqueous layers were neutralized with 1N aqueous hydrogen chloride and saturated aqueous sodium bicarbonate. Precipitates were collected by filtration, washed with water and dried under vacuum at 80° C. to give the titled compound (488 mg, 35% from methyl 4-(3-methylsulfinylphenyl)-3,4,5,6-2H-tetrahydropyran-4-carboxylate).

$^1$H NMR (CDCl$_3$) δ: 7.49–7.37 (7 H, m), 7.34–7.29 (1 H, m), 7.30 (1 H, d, J=1.10 Hz), 6.91 (1 H, d, J=1.10 Hz), 3.90–3.78 (2 H, m), 3.49–3.36 (2 H, m), 2.38–2.28 (2 H, m), 2.28 (3 H, s), 1.88–1.76 (2 H, m).

H. 4-[3-[4-(2-Methylimidazol-1-yl)phenylthio]phenyl]-3,4,5,6-tetrahydro-2H-pyran-4-carboxamide To a stirred suspension of 4-[3-[4-(2-methylimidazol-1-yl)phenylthio]phenyl]-3,4,5,6-tetrahydro-2H-pyran-4-carboxylic acid (217 mg, 0.55 mmol) at 0° C. was added oxalyl chloride (254 mg, 2.0 mmol). The resulting solution was stirred at 0° C. for 30 min and then at room temperature for 20 min. Volatiles were then removed by evaporation. The residue was added to a stirred aqueous ammonia solution (30 ml) and stirred for 1 hr. After cooling to 0° C., precipitates were collected by filtration, washed with water and dried to constant weight under vacuum at 80° C. to give the titled compound (207 mg, 96%).

$^1$H NMR (DMSO-d$_6$) δ: 7.49–7.26 (10 H,m), 7.10 (1 H, br s), 6.90 (1 H, d, J=1.10 Hz), 3.78–3.68 (2 H, m), 3.52–3.40 (2 H, m), 2.46–2.36 (2 H, m), 2.28 (3 H, s), 1.86–1.64 (2 H, m).

Example 9

4-[3-[4-(Pyrrol-1-ylmethyl)phenylthio]phenyl]-3,4,5,6-tetrahydro-2H-pyran-4-carboxamide A. Ethyl 4-[3-[4-(pyrrol-1-ylmethyl)phenylthio]phenyl]-3,4,5,6-tetrahydro-2H-pyran-4carboxylate (Claimed Compound)

The titled compound was obtained according to the procedure described in Example 8F for preparation of ethyl 4-[3-[4-(2-methylimidazol-1-yl)phenylthio]phenyl]-3,4,5,6-tetrahydro-2H-pyran-4-carboxylate using 4-(pyrrol-1-ylmethyl)phenyliodide (EP 488 602 A1) instead of 4-(2-methylimidazol-1-yl)phenyliodide.

$^1$H NMR (CDCl$_3$) δ: 7.38–7.34 (1 H, m), 7.28–7.18 (5 H, m), 7.04 (2 H, d, J=8.43 Hz), 6.68 (2 H, t, J=2.20 Hz), 6.19

(2 H, t, J=2.20 Hz), 5.05 (2 H, s), 4.12 (2 H, q, J=7.33 Hz), 3.96–3.86 (2 H, m), 3.59–3.49 (2 H, m), 2.50–2.42 (2 H, m), 1.99–1.85 (2 H, m), 1.16 (3 H, t, J=7.33 Hz).

B. 4-[3-[4-(Pyrrol-1-ylmethyl)phenylthio]phenyl]-3,4,5,6-tetrahydro-2H-pyran-4-carboxylic acid (Claimed Compound)

The titled compound was obtained according to the procedure described in Example 8G for the preparation of 4-[3-[4-(2-methylimidazol-1-yl)phenylthio]phenyl]-3,4,5,6-tetrahydro-2H-pyran-4-carboxylic acid using ethyl 4-[3-[4-(pyrrol-1-ylmethyl)phenylthio]phenyl]-3,4,5,6-tetrahydro-2H-pyran-4-carboxylate instead of ethyl-[3-[4-(2-methylimidazol-1-yl)phenylthio]phenyl]-3,4,5,6-tetrahydro-2H-pyran-4-carboxylate.

$^1$H NMR (CDCl$_3$) δ: 7.40–7.37 (1 H, m), 7.32–7.25 (4 H, m), 7.23–7.16 (1 H, m), 7.04 (2 H, d, J=8.43 Hz), 6.68 (2 H, t, J=2.20 Hz), 6.19 (2 H, t, J=2.20 Hz), 5.05 (2 H, s), 3.96–3.87 (2 H, m), 3.66–3.55 (2 H, m), 2.51–2.41 (2 H, m), 200–1.88 (2 H, m).

C. 4-[3-[4-(Pyrrol-1-ylmethyl)phenylthio]phenyl]-3,4,5,6-tetrahydro-2H-pyran-4-carboxamide A suspension of 4-[3-[4-(pyrrol-1-ylmethyl)phenylthio]phenyl]-3,4,5,6-tetrahydro-2H-pyran-4-carboxylic acid (0.36 g, 0.93 mmol), ammonium bicarbonate (0.44 g, 5.58 mmol) and 2-ethoxy-1-ethoxycarbonyl-1,2-dihydroquinoline (0.28 g, 1.12 mmol) in dichloromethane (20 ml) were stirred at room temperature overnight. Ammonium bicarbonate and 2-ethoxy-1-ethoxycarbonyl-1,2-dihydroquinoline were added until the acid was consumed. The reaction mixture was diluted with dichloromethane (50 ml) and washed with water (50 ml). The organic extract was washed with cold 1N hydrochloric acid (50 ml), water (50 ml) and saturated aqueous sodium bicarbonate (5 ml), water (50 ml) and brine (50 ml), dried (magnesium sulfate) and concentrated to dryness. Recrystallization of the residue from ethyl acetate afforded the titled compound (198 mg, 54%).

$^1$H NMR (DMSO-d$_6$) δ 7.38–7.25 (6 H, m), 7.18–7.03 (4 H, m), 7.80 (2 H, t, J=2.20 Hz), 6.02 (2 H, t, J=2.20 Hz), 5.09 (2 H, s), 3.77–3.66 (2 H, m), 3.50–3.38 (2 H, m), 2.42–2.32 (2 H, m), 1.82–1.68 (2 H, m).

Example 10

N-Methyl-4-[5-fluoro-3-[4-(2-methylimidazol-1-yl) benzyloxy]phenyl]-3,4,6-tetrahydro-2H-pyran-4-carboxamide The titled compound was prepared according to the procedure described in Example 5 except that aqueous methylamine (40%) was used in place of aqueous ammonia. Excess methyl amine was removed under reduced pressure, the residue was diluted with water (100 ml) and extracted with dichloromethane (2×100 ml). The combined extracts were dried (magnesium sulfate) and concentrated. The residue was recrystallized from ethyl acetate to give the titled compound as fine white solids.

$^1$H NMR (DMSO-d$_6$) δ: 7.69 (1 H, br s), 7.61 (2 H, d, J=8.43 Hz), 7.47 (2 H, d, J=8.43 Hz), 7.29 (1H, d, J=1.10 Hz), 6.91 (1 H, d, J=1.10 Hz), 6.90–6.80 (2 H, m), 6.79–6.70 (1 H, m), 5.17 (2 H, s), 3.75–3.65 (2 H, m), 3.48–3.36 (2 H, m), 2.55 (3 H, s), 2.41–2.31 (2 H, m), 2.29 (3 H, s), 1.90–1.77 (2 H, m).

Example 11

4-[5-Fluoro-3-[4-(2-methylimidazol-1-yl)benzyloxy] phenyl]-3,4,5,6-tetrahydro-2H-pyran-4-thiocarboxamide To a stirred solution of 4-[5-fluoro-3-[4-(2-methylimidazol-1-yl)benzyloxy]-phenyl]-3,4,5,6-tetrahydro-2H-pyran-4-carboxamide (Example 5) in THF (10 ml) was added phosphorus pentasulfide (236 mg, 0.53 mmol) and sodium bicarbonate (176 mg, 2.1 mmol). The resulting mixture was heated at 40° C. for 4 hr. The mixture was concentrated in vacuo. To the residue was added water (100 ml) and the mixture was extracted with dichloromethane (2×100 ml). The combined organic extracts were dried over sodium sulfate and concentrated in vacuo. The residue was purified on column chromatography (LiChropprep —NH2) and then by p-TLC eluting with dichloromethane-methanol (10:1) to afford 38 mg of the titled compound as white solids.

$^1$H-NMR (CDCl$_3$) δ: 7.67–7.49 (3 H, m), 7.39–7.29 (2 H, m), 7.03 (1 H, d, J=1.47 Hz), 7.01 (1 H, d, J=1.46 Hz), 6.98–6.62 (4 H, m), 5.09 (2 H, s), 3.95–3.80 (2 H, m), 3.70–3.54 (2 H, m), 2.70–2.55 (2 H, m), 2.37 (3 H, s), 2.30–2.14 (2 H, m). IR (KBr) ν: 1620, 1590, 1520, 1420, 1140 cm−1 mp: 167–170° C.

Example 12

4-[3-[4-(2-Methylimidazol-1-ylmethyl)phenlthio] phenyl]-3,4,5,6-tetrahydro-2H-pyran-4-carboxamide A. 4-[(2-Methylimidazol-1-yl)methyl]phenyliodide A mixture of 2-methylimidazole (0.66 g, 8.0 mmol), 4-iodobenzyl bromide (J. Am. Chem. Soc, 1949, 71, 3360) (2.38 g, 8.0 mmol) and potassium carbonate (2.21 g, 16 mmol) in acetonitrile (100 ml) was stirred at reflux for 15 hrs. After cooling, precipitates were filtered off and the filtrate was concentrated to dryness. The residue was partitioned between ether (100 ml) and water (100 ml). The ethereal layer was separated, washed with brine (100 ml), dried (magnesium sulfate) and concentrated. Purification by column chromatography (silica-gel, 50 g; methanol in dichloro-methane, increasing the ratio of methanol from 0% to 5%) yielded the titled compound (1.05 g, 44%).

$^1$H NMR (CDCl$_3$) δ: 7.67 (2 H, d, J=8.42 Hz), 6.96 (1 H, d, J=1.10 Hz), 6.82 (1 H, d, J=1.10 Hz), 6.79 (2 H, d, J=8.42 Hz), 4.99 (2 H, s), 2.32 (3 H, s).

B. Ethyl 4-[3-[4-[(2-methylimidazol-1-yl)methyl] phenylthio]phenyl]-3,4,5,6-tetrahydro-2H-pyran-4-carboxylate (Claimed Compound)

The titled compound was obtained according to the procedure described in Example 8F for preparation of ethyl 4-[3-[4-(2-methylimidazo-1-yl)phenylthio]phenyl]-3,4,5,6-tetrahydro-2H-pyran-4-carboxylate using 4-[(2-methylimidazol-1-yl)methyl]-phenyliodide instead of 4-(2-methylimidazol-1-yl)phenyliodide.

$^1$H NMR (CDCl$_3$) δ: 7.40–6.82 (10 H, m), 5.27 (2 H, s), 4.13 (2 H, q, J=6.96 Hz), 3.96–3.86 (2 H, m), 3.61–3.47 (2 H, m), 2.52–2.42 (2 H, m), 2.33 (3 H, m), 1.99–1.87 (2 H, m), 1.25 (3 H, t, J=6.96 Hz).

C. 4-[3-[4-(2-Methylimidazol-1-ylmethyl)phenylthio] phenyl]-3,4,5,6-tetrahydro-2H-pyran-4carboxylic acid (Claimed Compound)

The titled compound was obtained according to the procedure described in Example 8G for the preparation of 4-[3-[4-(2-methylimidazol-1-yl)phenylthio]phenyl]-3,4,5,6-tetrahydro-2H-pyran-4-carboxylic acid using ethyl 4-[3-[4-[(2-methylimidazol-1-yl)methyl]phenylthio]-phenyl]-3,4,5,6-tetrahydro-2H-pyran-4-carboxylate instead of ethyl 4-[3-[4-(2-methylimidazol-1-yl)phenylthio]phenyl]-3,4,5,6-tetrahydro-2H-pyran-4-carboxylate.

$^1$H NMR (CDCl$_3$) δ: 7.56–7.52 (1 H, m), 7.45–7.40 (1H, m), 7.36–7.23 (2 H, m), 7.19 (2 H, d, J=8.42 Hz), 6.95 (1 H, d, J=1.46 Hz), 6.91 (2 H, d, J=8.42 Hz), 6.79 (1 H, d, J=1.46 Hz), 4.98 (2 H, s), 3.96–3.86 (2 H, m), 3.74–3.62 (2 H, m), 2.57–2.47 (2 H, m), 2.31 (3 H, s), 1.97–1.83 (2 H, m).

D. 4-[3-[4-(2-Methylimidazol-1-ylmethyl)phenylthio] phenyl]-3,4,5,6-tetrahydro-2H-pyran-4carboxamide The titled compound was obtained according to the procedure described in Example 9C for the preparation of 4-[3-[4-[(pyrrol-1-yl)methyl]phenylthio]phenyl]-3,4,5,6-tetrahydro-2H-pyran-4-carboxamide using 4-[3-[4-(2-methylimidazol-1-yl-methyl)phenyl-thio]phenyl]-3,4,5,6-tetrahydro-2H-pyran-4-carboxylic acid instead of 4-[3-[4-(pyrro-1-ylmethyl)phenylthio]phenyl]-3,4,5,6-tetrahydro-2H-pyran-4-carboxylic acid.

$^1$H NMR (CDCl$_3$) δ: 7.39–7.36 (1 H,m), 7.37–7.19 (5 H, m), 6.99 (2 H, d, J=8.79 Hz), 6.96 (1 H, d, J=1.47 Hz), 6.85 (1 H, d, J=1.47 Hz), 5.20 (2 H, br s), 5.04 (2 H, s), 3.82–3.72 (4 H, m), 2.34 (3 H, s), 2.35–2.29 (2 H, m), 2.09–1.97 (2 H, m).

Example 13

1-[5-Fluoro-3-[4-(2-methylimidazol-1-yl)benzyloxy] phenyl]cyclohexane-1-carboxamide A. Ethyl 1-(3-benzyloxy-5-fluorophenyl)cyclohexane-1-carboxylate The titled compound was prepared from ethyl 3-benzyloxy-5-fluorophenylacetate according to the procedure described in Example 2F except that 1,5-dibromopentane was used in place of bis(2-chloroethyl) ether.

$^1$H NMR (CDCl$_3$) δ: 7.48–7.27 (5 H, m), 6.84–6.80 (1 H, m), 6.73 (1 H, ddd, J=10, 2.2, 2.2 Hz), 6.56 (1 H, ddd, J=10, 2.2, 2.2 Hz), 5.02 (2 H, s), 4.11 (2 H, q, J=7.0 Hz), 2.49–2.32 (2 H, m), 1.77–1.35 (8 H, m), 1.18 (3 H, t, J=7.0 Hz).

B. Ethyl 1-(5-fluoro-3-hydroxyphenyl)cyclohexane-1-carboxylate

The titled compound was prepared from ethyl 1-(3-benzyloxy-5-fluorophenyl)-cyclohexane-1-carboxylate according to the procedure described in Example 2G.

$^1$H NMR (CDCl$_3$) δ: 6.72–6.63 (2 H, m), 6.47 (1 H, ddd, J=2.2, 2.2, 10 Hz), 4.13 (2 H, q, J=7.0 Hz), 2.48–2.33 (2 H, m), 1.75–1.35 (8 H, m), 1.20 (3 H, t, J=7.0 Hz).

C. Ethyl 1-[5-fluoro-3-[4-(2-methylimidazol-1-yl) benzyloxy]phenyl]cyclohexane-1-carboxylate (Claimed Compound)

The titled compound was prepared from ethyl 1-(5-fluoro-3-hydroxyphenyl)-cyclohexane-1-carboxylate according to the procedure described in Example 2H.

$^1$H NMR (CDCl$_3$) δ: 7.55 (2 H, d, J=8.4 Hz), 7.33 (2 H, d, J=8.4 Hz), 7.04 (1 H, d, J=1.5 Hz), 7.01 (1 H, d, J=1.5 Hz), 6.86–6.83 (1 H, m), 6.76 (1 H, ddd, J=2.2, 2.2, 9.7 Hz), 6.58 (1 H, ddd, J=2.2, 2.2, 10 Hz), 5.08 (2 H, s), 4.12 (2 H, q, J=7.0 Hz), 2.49–2.38 (2 H, m), 2.38 (3 H, s), 1.79–1.58 (6 H, m), 1.53–1.32 (2 H, m), 1.19 (3 H, t, J=7.0 Hz).

D. 1-[5-Fluoro-3-[4-(2-methylimidazol-1-yl)benzyloxy] phenyl]cyclohexan-1-carboxamide The desired compound was prepared from ethyl 1-[3-fluoro-5-[4-(2-methylimidazol-1-yl)benzyloxy]phenyl] cyclohexan-1-carboxylate according to the procedure described in Example 5.

$^1$H NMR (CDCl$_3$) δ: 7.53 (2 H, d, J=8.1 Hz), 7.22 (2 H, d, J=8.1 Hz), 7.08 (1 H, s), 6.96 (1 H, s), 6.95 (1 H, m), 6.83 (1 H, ddd, J=2.2, 2.2, 9.5 Hz), 6.56 (1 H, ddd, J=2.2, 2.2, 9.5 Hz), 6.10 (2 H, br.s), 5.11 (2 H, s), 2.60–2.35 (2 H, m), 2.33 (3 H, s), 1.79–1.50 (8 H, m).

Example 14

1-[5-Fluoro-3-[4-(2-methylimidazol-1-yl)benzyloxy] phenyl]cyclopent-3-ene-1-carboxamide A. Methyl 5-fluoro-3-methoxyphenylacetate To a stirred mixture of methyl 5-fluoro-3-hydroxyphenylacetate (3.3 g, 15.7 mmol) and potassium carbonate (1.82 g, 50 mmol) in DMF (30 ml) was added methyl iodide (1.82 g, 50 mmol) at room temperature and the reaction mixture was stirred overnight. Then the mixture was diluted with water (50 ml) and extracted with ether. The combined extracts were washed with water and brine, dried (MgSO4) and concentrated in vacuo. The residue was purified by column chromatography (SiO2, 150 g; hexane/ethyl acetate (10/1)) afforded 495 mg (55%) of methyl 5-fluoro-3-methoxyphenylacetate as a colorless oil.

$^1$H NMR (CDCl$_3$) δ: 6.64–6.57 (2 H, m), 6.53 (1 H, ddd, J=2.2, 2.2, 11 Hz), 3.79 (3 H, s), 3.71 (3 H, s), 3.57 (2 H, s).

B. Methyl 1-(3-Fluoro-3-methoxyphenyl)cyclopent-3-ene-1-carboxylate

To a stirred solution of methyl 5-fluoro-3-methoxyphenylacetate (708 mg, 3.6 mmol) in THF (10 ml) was added a 1.0 M solution of potassium t-butoxide in THF (4.0 ml, 4.0 mmol) at −30° C. over 0.25 hr. After stirring for 1 h at the same temperature, a solution of cis-1,4-dichlorobut-2-ene (526 mg, 4.0 mmol) in THF (2 ml) was added dropwise and the reaction mixture was warmed to room temperature over 2 hr period. The reaction mixture was cooled to −30° C., and 1.0 M solution of potassium t-butoxide in THF (4.0 ml, 4.0 mmol) was added and the mixture was stirred overnight at room temperature. The reaction was quenched by the addition of saturated aqueous ammonium chloride solution and extracted with ethyl acetate. The combined extracts were washed with brine, dried with MgSO$_4$ and concentrated in vacuo. Purification by column chromatography (SiO$_2$, 150 g; hexane/ethyl acetate (20/1)) afforded 495 mg (55%) of methyl 1-(5-fluoro-3-methoxyphenyl)cyclopent-3-ene-1-carboxylate as a colorless oil.

$^1$H NMR (CDCl$_3$) δ: 6.67–6.60 (2 H, m), 6.49 (1 H, ddd, J=11, 2.2, 2.2 Hz), 5.75 (2 H, s), 3.78 (3 H, s), 3.66 (3 H, s),3.36 (2 H, d, J=15 Hz), 2.72 (2 H, d, J=15 Hz).

C. Methyl 1-(5-fluoro-3-hydroxyphenyl)cyclopent-3-ene-1-carboxylate

To a stirred solution of methyl 1-(5-fluoro-3-methoxyphenyl)cyclopent-3-ene-1-carboxylate (495 mg, 2.0 mmol) in dry dichloromethane (10 ml) was added a 1.0M solution of boron tribromide in dichloromethane (10 ml, 10 mmol) at −78° C. and the mixture stirred for 1 hr at the same temperature. The reaction mixture was quenched by the addition of water (20 ml) and the resulted mixture acidified with 1.0N aqueous hydrochloric acid, and extracted with ethyl acetate. The organic phase was washed with brine, dried and concentrated under reduced pressure. The residue was dissolved in a mixture of methanol (5 ml) and toluene (15 ml) and a 2.0M solution of trimethylsilyldiazomethane in hexane (2 ml, 4 mmol) was added at ambient temperature with stirring. After 0.5 hr, the reaction mixture was partitioned between ethyl acetate and water, the organic phase was separated and the aqueous phase was extracted with ethyl acetate. The combined organic phase was washed with brine, dried with MgSO$_4$ and concentrated in vacuo. The resultant oil was purified by column chromatography (SiO$_2$, 150 g; hexane/ethyl acetate (4/1)) to afford 407 mg (87%) of methyl 1-(5-fluoro-3-hydroxyphenyl)cyclopent-3-ene-1-carboxylate white crystals.

$^1$H NMR (CDCl$_3$) δ: 6.64–6.57 (2 H, m), 6.46 (1 H, ddd, J=9.9, 2.2, 2.2 Hz), 5.75 (2 H, s), 5.68 (1 H, br.s), 3.67 (3 H, s),3.35 (2 H, d, J=15 Hz), 2.71 (2 H, d, J=15 Hz).

D. 1-[5-Fluoro-3-[4-(2-methylimidazol-1-yl)benzyloxy]phenyl]cyclopent-3-ene-1-carboxamide Methyl 1-(5-fluoro-3-hydroxyphenyl)cyclopent-3-ene-1-carboxylate was converted to the titled compound as described for the preparation of 4-[5-fluoro-3-[4-(2-methylimidazol-1-yl)benzyloxy]phenyl]-3,4,5,6-tetrahydro-2H-pyran-4-carboxamide (Example 5).

$^1$H NMR (DMSO-d$_6$) δ: 7.62 (2 H, d, J=8.4 Hz), 7.48 (2 H, d, J=8.4 Hz), 7.30 (1 H, d, J=2.2 Hz), 6.92 (1 H, d, J=2.2 Hz), 6.92–6.83 (1 H, m), 6.79–6.75 (1 H, m), 6.74–6.67 (1 H, m), 5.76 (2 H, s), 5.18 (2 H, s), 3.27 (2 H, d, J=15 Hz), 2.62 (2 H, d, J=15 Hz), 2.30 (3 H, s).

Example 15

4-[3-[4-(2-methylimidazol-1-yl)benzylox]phenyl]-3,4,5,6-tetrahydro-2H-pyran-4-carboxamide A. 4-(3-Benzyloxyphenyl)-3,4,5,6-tetrahydro-2H-pyran-4-carboxylic acid The titled compound was prepared according to the procedure described in Example 4 except that ethyl 4-(3-benzyloxyphenyl)-3,4,5,6-tetrahydro-2H-pyran-4-carboxylate (EP 462830 A2) was used in place of ethyl 4-[5-fluoro-3-[4-(2-methyl-imidazol-1-yl)benzyloxy]phenyl]-3,4,5,6-tetrahydro-2H-pyran-4-carboxylate.

$^1$H-NMR (CDCl$_3$) δ: 7.68–7.22 (6 H, m), 7.22–7.01 (2 H, m), 6.95–6.82 (1 H, m), 5.09 (2 H,s), 4.10–3.80 (2 H, m), 3.80–3.41 (2 H, m), 2.70–2.25 (2 H, m), 2.19–1.75 (2 H, m).

B. 4-(3-Benzyloxyphenyl)-3,4,5,6-tetrahydro-2H-pyran-4-carbox amide

The titled compound was prepared according to the procedure described in Example 5 except that 4-(3-benzyloxyphenyl)-3,4,5,6-tetrahydro-2H-pyran-4-carboxylic acid was used in place of 4-[5-fluoro-3-[4-(2-methylimidazol-1-yl)-benzyloxy]phenyl]-3,4,5,6-tetrahydro-2H-pyran-4-carboxylic acid.

$^1$H-NMR (CDCl$_3$) δ: 7.52–7.30 (6 H, m), 7.04–6.99 (2 H, m), 6.98–6.88 (1 H, m), 5.19 (2 H, br s), 5.07 (2 H, s), 3.91–3.74 (4 H, m), 2.43–2.31 (2 H, m), 2.19–2.02 (2 H, m).

C. 4-(3-Hydroxyphenyl)-3,4,5,6-tetrahydro-2H-pyran-4-carboxamide

The titled compound was prepared according to the procedure described in Example 2G except that 4-(3-benzyloxyphenyl)-3,4,5,6-tetrahydro-2H-pyran-4-carboxamide was used in place of ethyl 4-(3-benzyloxy-5-fluorophenyl)-3,4,5,6-tetrahydro-2H-pyran-4-carboxylate.

$^1$H-NMR (CDCl$_3$) δ: 9.40 (1 H, br s), 7.11 (1 H, t, J=8.1 Hz), 6.97 (1H, s), 6.78 (1 H, d, J=7.7 Hz), 6.62 (1 H, d, J=8.4 Hz), 3.68–3.82 (2 H, m), 3.58–3.40 (2 H, m), 2.44–2.27 (2 H, m), 0.82–0.68 (2 H, m).

D. 4-[3-[4-(2-methylimidazol-1-yl)benzyloxy]phenyl]-3,4,5,6-tetrahydro-2H-pyran-4-carboxamide 4-(3-Hydroxyphenyl)-3,4,5,6-tetrahydro-2H-pyran-4-carboxamide was reacted with 4-(2-methylimidazol-1-yl)benzyl chloride hydrochloride according to the procedure described in Example 2H to give the titled compound. mp: 183.0–186.0° C.

$^1$H-NMR (CDCl$_3$) δ: 7.60–7.57 (2 H, m), 7.41–7.32 (3 H, m), 7.09–7.00 (4 H, m), 6.98–6.91 (1 H, m), 5.36–5.22 (2 H, br s), 5.13 (2 H, s), 3.89–3.76 (4 H, m), 2.44–2.33 (5 H, m), 2.19–2.02 (2 H, m). IR (KBr) ν: 3400, 3200, 2900, 1680, 1520, 1420, 1380, 1310, 1250, 1170, 1100 cm$^{-1}$.

Example 16

1-[3-[4-(2-Methylimidazol-1-yl)benzyloxy]phenyl]cyclopentane-1-carboxamide

A. Ethyl 1-[3-benzyloxyphenyl]cyclopentane-1-carboxylate

The titled compound was prepared according to the procedure described in Example 2F except that ethyl 1,4-dibromobutane was used in place of bis(2-chloroethyl)ether and 3-benzyloxyphenylacetate was used in place of ethyl 3-(benzyloxy)-5-fluorophenylacetate.

$^1$H-NMR (CDCl$_3$) δ: 7.52–7.30 (5 H, m), 7.30–7.20 (1 H, m), 7.09–6.94 (2 H, m), 6.91–6.82 (1 H, m), 5.05 (2 H, s), 4.06 (2 H, q, J=7.0 Hz), 2.72–2.56 (2 H, m), 1.99–1.83 (2 H, m), 1.82–1.64 (4 H, m), 1.15 (3 H, t, J=7.0 Hz).

B. 1-[3-Benzyloxyphenyl]cyclopentane-1-carboxylic acid

The titled compound was prepared according to the procedure described in Example 4 except that ethyl 1-[3-benzyloxyphenyl]cyclopentane-1-carboxylate was used in place of ethyl 4-[5-fluoro-3-[4-(2-methylimidazol-1-yl)benzyloxy]phenyl]-3,4,5,6-tetrahydro-2H-pyran-4-carboxylate.

$^1$H-NMR (CDCl$_3$) δ: 7.56–7.21 (6 H, m), 7.09–7.00 (2 H, m), 6.88 (1H, m), 5.03 (2 H,s), 2.71–2.53 (2 H, m), 2.00–1.88 (2 H, m), 1.87–1.66 (4 H, m).

C. 1-[3-Benzyloxyphenyl]cyclopentane-1-carboxamide

The titled compound was prepared according to the procedure described in Example 5 except that 1-[3-benzyloxyphenyl]cyclopentane-1-carboxylic acid was used in place of 4-[5-fluoro-3-[4-(2-methylimidazol-1-yl)benzyloxy]phenyl]-3,4,5,6-tetrahydro-2H-pyran-4-carboxylic acid.

$^1$H-NMR (CDCl$_3$) δ: 7.50–7.22 (6 H, m), 6.92 (2 H, s), 6.88 (1 H, m), 5.48–5.10 (2 H, br s), 5.04 (2 H, s), 2.52–2.36 (2 H, m), 2.12–1.95 (2 H, m), 1.92–1.55 (4 H, m).

D. 1-[3-Hydroxyphenyl]cyclopentane-1-carboxamide

The titled compound was prepared according to the procedure described in Example 2G except that 1-[3-benzyloxyphenyl]cyclopentane-1-carboxamide was used in place of ethyl 4-(3-benzyloxy-5-fluorophenyl)-3,4,5,6-tetrahydro-2H-pyran-4-carboxylate.

$^1$H-NMR (CDCl$_3$) δ: 9.84 (1 H, br s), 7.59 (1 H, t, J=7.7 Hz), 7.45 (1H, s), 7.30 (1 H, s), 7.10 (1 H, d, J=8.4 Hz), 3.06–2.88 (4 H, m), 2.30–2.00 (4 H, m).

E. 1-[3-[4-(2-Methylimidazol-1-yl)benzyloxy]phenyl]cyclopentane-1-carboxamide 1-(3-Hydroxyphenyl)cyclopentane-1-carboxamide was reacted with 4-(2-methyl-imidazol-1-yl)benzyl chloride hydrochloride according to the procedure described in Example 2H to give the titled compound. mp: 163.0–164.0° C.

$^1$H-NMR (CDCl$_3$) δ: 7.56 (2 H, d, J=8.0 Hz), 7.50–7.31 (3 H, m), 7.18–6.99 (4 H, m), 6.97–6.88 (1 H, m), 5.45–5.20 (2 H, br s), 5.11 (2 H, s), 2.60–2.30 (2 H, m), 2.38 (3 H, s), 2.19–1.60 (6 H, m). IR (KBr) ν: 3400, 3200, 2950, 1670, 1610, 1580, 1520, 1420, 1370, 1310, 1290, 1260, 1060 cm$^{-1}$.

Example 17

4-[5-Fluoro-3-[4-(2-methylimidazol-1-yl)benzyloxy]phenyl]-3,4,5,6-tetrahydro-2H-pyran-4-carboxamide hydrochloride 4-[5-Fluoro-3-[4-(2-methylimidazol-1-yl)benzyloxy]phenyl]-tetrahydro-2H-pyran-4-carboxamide (39 mg, 0.1 mmol) was dissolved in 10% hydrogen chloridemethanol (2 ml). After stirring for 10 min, volatiles were removed by evaporation and the resulting residue recrystallized from ethanol to give the titled compound (24 mg, 57%) as white solids.

¹H-NMR (DMSO-d₆) δ: 7.87 (1 H, s), 7.78–7.63 (5 H, m), 7.25 (1 H, s), 7.08 (1 H, s), 6.88–6.74 (3 H, m), 5.23 (2 H, s), 3.80–3.66 (2 H, m), 3.60–3.42 (2 H, m), 2.54 (3 H, s), 2.50–2.33 (2 H, m), 1.88–1.69 (2 H, m).

Example 18

4-[3-[4-(2-methylimidazol-1-yl) phenyl]thiophenyl]-3,4,5,6-tetrahydro-2H-pyran-4-carboxamide hydrochloride The same procedure as described in Example 17, was used except that 4-[3-[4-(2-methylimidazol-1-yl)phenyl]thiophenyl]-3,4,5,6-tetrahydro-2H-pyran-4-carboxamide was used instead of 4-[5-fluoro-3-[4-(2-methylimidazol-1-yl)benzyloxy]-phenyl]-3,4,5,6-tetrahydro-2H-pyran-4-carboxamide. mp: 216–222° C. (decomposition)

¹H-NMR (DMSO-d₆) δ: 7.86 (1H, d, J=2.20 Hz), 7.75 (1 H, d, J=2.20 Hz), 7.59 (1 H, d, J=8.79 Hz), 7.53–7.50 (1 H, m), 7.49–7.33 (3 H, m), 7.41 (1 H, d, J=8.79 Hz), 7.32 (1 H, br s), 7.10 (1 H, br s), 3.78–3.69 (2 H, m), 3.51–3.43 (2 H, m), 2.51 (3 H, s), 2.48–2.37 (2 H, m), 1.88–1.74 (2 H, m).

Example 19

4-[3-[4-(2-methylimidazol-1-yl)phenylthio]phenyl]-3,4,5,6-tetrahydro-2H-pyran-4-carboxamide hemifumarate 4-[3-[4-(2-methylimidazol-1-yl)phenylthio]phenyl]-3,4,5,6-tetrahydro-2H-pyran-4-carboxamide (39 mg, 0.1 mmol) and fumaric acid (12 mg, 0.1 mmol) were dissolved in methanol (3 ml). After stirring for 10 min, volatiles were removed by evaporation and the resulting residue recrystallized from 2-propanol to give the titled compound (40 mg, 78%) as white solids. mp: 183.5–184.9° C.

¹H-NMR (DMSO-d₆) δ: 7.48–7.34 (7 H, m), 7.32–7.25 (3 H, m), 7.08 (1 H, s), 6.93 (1 H, s), 6.63–6.61 (1 H, m), 3.79–3.64 (2 H, m), 3.55–3.37 (2 H, m), 2.45–2.36 (2 H, m), 2.28 (3 H, s), 1.84–1.72 (2 H, m). IR (KBr) ν: 3400, 3200, 2950, 1670, 1610, 1580, 1520, 1420, 1370, 1310, 1290, 1260, 1060 cm⁻¹.

Example 20

1-[3-[4-(2-Methylimidazol-1-yl)benzyloxy]phenyl]cyclobutane-1-carboxamide

A. 1-Cyano-1-(3-methoxyphenyl)cyclobutane

To a solution of (3-methoxyphenyl)acetonitrile (3.0 g, 20.0 mmol) in DMSO (120 ml) was added 3 drops of 15-crown-5 and sodium hydride (60% w/w dispersion in mineral oil, 1.6 g) at room temperature and the reaction mixture was stirred for 30 min. Sodium iodide (3.6 g 24 mmol) and 1,3-dibromopropane (8.0 g 40 mmol) were added and the mixture stirred overnight. 2N HCl (50 ml) was added and the mixture extracted with ether (100 ml×2). The combined extracts were washed with water (100 ml×2) and brine (100 ml ), dried (MgSO₄) and concentrated in vacuo. The residue was purified by column chromatography (SiO₂, 300 g; hexane/ethyl acetate (20/1)) to afford 2.10 g (56%) of titled compound as a colorless oil.

¹H NMR (CDCl₃) δ: 7.32 (1 H, dd, J=13.9, 5.9 Hz), 7.00 (1 H, m), 6.93 (1 H, J=2.2, 2.2 Hz), 6.85 (1 H, dd, J=8.1, 2.6 Hz), 3.85 (3 H, s), 2.90–2.77 (2 H, m), 2.71–2.58 (2 H, m), 2.54–2.31 (1 H, m), 2.18–2.00 (1 H, m).

B. 1-Cyano-1-(3-hydroxyphenyl)cyclobutane

To a stirred solution of 1-cyano-1-(3-methoxyphenyl)cyclobutane (1.93 g, 10 mmol) in dry dichloromethane (50 ml) was added a 1.0 M solution of boron tribromide in dichloromethane (22 ml, 22 mmol) at 0° C. and the mixture stirred for 30 min at the same temperature, then overnight at room temperature. The reaction mixture was quenched by the addition of water (100 ml) and extracted with dichloromethane (50 ml×2). The organic phase was washed with brine (50 ml), dried (MgSO₄) and concentrated in vacuo to afford 1.70 g (100%) of the titled compound as a clear brown oil.

¹H NMR (CDCl₃) δ: 7.29 (1 H, d, J=1.8 Hz), 6.98 (1 H, m), 6.83 (1 H, m), 6.78 (1 H, br.s), 2.91–2.78 (2 H, m), 2.78–2.53 (2 H, m), 2.52–2.33 (1 H, m), 2.20–1.99 (1 H, m).

C. 1-Cyano-1-[3-[4-(2-methylimidazol-1-yl)benzyloxy]phenyl]cyclobutane (Claimed Compound)

A mixture of 1-cyano-1-(3-hydroxyphenyl)cyclobutane (1.76 g, 10 mmol), 4-(2-methylimidazol-1-yl) benzylchloride hydrochloride (2.10 g, 10 mmol) and potassium carbonate (6.90 g, 50 mmol) in DMF (80 ml) were stirred together at 80° C. for 3 hrs. Water (200 ml) was added and the mixture extracted with ethyl acetate/benzene (2/1, 100 ml×2), washed with water (100 ml×2), brine (100 ml), dried (MgSO₄) and concentrated in vacuo. The residue was purified by column chromatography (SiO₂, 150 g; dichloromethane/methanol (20/1)) to afford 2.90 g (84%) of the titled compound as a clear yellow oil.

¹H NMR (CDCl₃) δ: 7.60 (2 H, d, J=8.2 Hz), 7.44–7.30 (3H, m), 7.13–6.88 (5 H, m), 5.18 (2H, s), 2.93–2.78 (2 H, m), 2.73–2.58 (2 H, m), 2.52–2.30 (4 H, m), 2.20–2.00 (1H, m).

D. 1-[3-[4-(2-methylimidazol-1-yl)benzyloxy]phenyl]cyclobutane-1-carboxamide

To a solution of 1-cyano-1-[3-[4-(2-methylimidazol-1-yl)benzyloxy]phenyl]-cyclobutane (2.90 g, 8.4 mmol) in DMSO (5 ml) cooled to 0° C. was added 30% H₂O₂ (2.0 ml) and potassium carbonate (0.4 g). The mixture was allowed to warm to room temperature and stirred overnight, and then stirred for 6 hrs at 60° C. Water (100 ml) was added and the mixture extracted with ethyl acetate (100 ml×3). The combined organic layers were extracted with 2N HCl (100 ml×2) and the aqueous layer washed with ethyl acetate (100 ml×3). The aqueous acidic layer was basified to pH=9 with 5N NaOH (150 ml) and extracted with ethyl acetate (100 ml×3). The combined organic extracts were washed with water (100 ml), brine (100 ml), dried (MgSO₄) and concentrated in vacuo to afford crude product as white solid. Recrystallization from ethyl acetate gave 2.13 g (70%) of the titled compound as a white solid.

¹H NMR (CDCl₃) δ: 7.56 (2 H, d, J=8.4 Hz), 7.36–7.29 (3 H, m), 7.08–6.87 (5 H, m), 5.20 (2 H, br.s), 5.12 (2 H, s), 2.91–2.78 (2 H, m), 2.56–2.42 (2 H, m), 2.38 (3 H, s), 2.28–2.10 (1 H, m), 1.98–1.82 (1 H, m).

Example 21

1-[3-[4-(2-methylimidazol-1-yl)benzyloxy]phenyl]cyclopropane-1-carboxamide

The titled compound was prepared according to the procedure described for 1-[3-[4-(2-methylimidazol-1-yl)benzyloxy]phenyl]cylobutane-1-carboxamide except that 1,2-dibromnoethane was used in place of 1,3-dibromopropane (Example 20).

¹H NMR (CDCl₃) δ: 7.56 (2 H, d, J=8.4 Hz), 7.37–7.28 (3 H, m), 7.12–7.07 (2 H, m), 7.04 (1 H, d, J=1.5 Hz), 7.01 (1 H, d, J=1.5 Hz), 6.95 (1 H, ddd, J=8.1, 1.8, 0.7 Hz), 5.80 (1 H, br.s), 5.42 (1 H, br.s), 2.38 (3 H, s), 1.68–1.56 (2 H, m), 1.17–1.06 (2 H, m).

Example 22

4-[5-Fluoro-3-[2-fluoro-4-(2-methylimidazol-1-yl)benzyloxy]phenyl]-3,4,5,6-tetrahydro-2H-pyran-4-carboxamide A. 4-[3-(Benzyloxy)-5-fluorophenyl]-3,4,5,6-tetrahydro-2H-pyran-4-carboxylic acid The titled compound was prepared according to the procedure described in Example 4 except that ethyl 4-[3-(benzyloxy)-5-fluorophenyl]-3,4,5,6-tetrahydro-2H-pyran-4-carboxylate was used in place of ethyl 4-[5-fluoro-3-[4-(2-methylimidazol-1-yl)benzyloxy]phenyl]-3,4,5,6-tetrahydro-2H-pyran-4-carboxylate.

$^1$H NMR (CDCl$_3$) δ: 7.49–7.29 (5 H, m), 6.87–6.80 (1 H, m), 6.74 (1 H, ddd, J=1.8, 2.2, 9.9 Hz), 6.62 (1 H, d, 2.2, 2.2, 10.3 Hz), 5.02 (2 H, s), 4.00–3.85 (2 H, m), 3.70–3.50 (2 H, m), 2.52–2.38 (2 H, m), 2.04–1.85 (2 H, m).

B. 4-[3-(Benzyloxy)-5-fluorophenyl]-3,4,5,6-tetrahydro-2H-pyran-4-carboxamide

The titled compound was prepared according to the procedure described in Example 5 except that 4-[3-(benzyloxy)-5-fluorophenyl]-3,4,5,6-tetrahydro-2H-pyran-4-carboxylic acid was used in place of 4-[5-fluoro-3-[4-(2-methylimidazol-1-yl)benzyloxy]phenyl]-3,4,5,6-tetrahydro-2H-pyran-4-carboxylic acid.

$^1$H NMR (CDCl$_3$) δ: 7.48–7.31 (5 H, m), 6.82–6.76 (1 H, m), 6.71 (1H, ddd, J=1.8, 1.8, 9.9 Hz), 6.65 (1 H, ddd, J=2.2, 2.2, 10.3 Hz), 5.23 (2 H, br s), 5.04 (2 H, s), 3.85–3.70 (4 H, m), 2.40–2.26 (2 H, m), 2.10–1.95 (2 H, m).

C. 4-[5-Fluoro-3-hydroxyphenyl]-3,4,5,6-tetrahydro-2H-pyran-4-carboxamide

The titled compound was prepared according to the procedure described in Example 2G except that 4-[5-fluoro-3-(benzyloxy)phenyl]-3,4,5,6-tetrahydro-2H-pyran-4-carboxamide was used in place of ethyl 4-(5-fluoro-3-benzyloxyphenyl)-3,4,5,6-tetrahydro-2H-pyran-4-carboxylate.

$^1$H NMR (CDCl$_3$) δ: 9.32 (1 H, br s), 6.75–6.45 (3 H, m), 6.13 (1 H, br s), 5.83 (1 H, br s), 3.90–3.58 (4 H, m), 2.47–2.30 (2 H, m), 2.10–1.90 (2 H, m).

D. 4-[5-Fluoro-3-[2-fluoro-4-(2-methylimidazol-1-yl)benzyloxy]phenyl]-3,4,5,6-tetrahydro-2H-pyran-4-carboxamide 4-(5-Fluoro-3-hydroxyphenyl)-3,4,5,6-tetrahydro-2H-pyran-carboxamide was reacted with 2-fluoro-4-(2-methylimidazol-1-yl)benzyl chloride hydrochloride according to the procedure described in Example 2H to give the titled compound in 41% yield as a white powder.

$^1$H NMR (CDCl$_3$) δ: 7.63 (1 H, dd, J=7.7, 8.1 Hz), 7.20–6.98 (4 H, m), 6.89–6.60(3 H, m), 5.41 (2 H, br s), 5.14 (2 H, s), 3.90–3.70 (4 H, m), 2.46–2.28 (5 H, m), 2.14–1.98 (2 H, m). IR (KBr) ν 3310, 3165, 1687, 1619, 1590, 1519, 1456, 1415.

Example 23

4-[2,5-Difluoro-3-[4-(2-methylimidazol-1-yl)benzyloxy]phenyl]-3,4,5,6-tetrahydro-2H-pyran-4-carboxamide A. O-tert-Butyldimethylsilyl-2,5-difluorophenol To a stirred solution of 2,5-difluorophenol (15.1 g, 116 mmol) in DMF (100 ml) was added sodium hydride (60% W/W dispersion in mineral oil; 5.13 g, 139 mmol) with ice-cooling. After stirring for 30 min, tert-butyldimethylsilyl chloride (17.5 g, 0.116 mmol) was added and stirring was continued for an additional 1 hr. The mixture was poured into water (200 ml) and extracted with ether (300 ml). The extract was washed with brine (200 ml), dried (sodium sulfate) and solvent removed by evaporation to give 26.65 g (94%) of the titled compound as a colorless oil.

$^1$H NMR (CDCl$_3$) δ: 7.05–6.91 (1 H, m), 6.70–6.52 (2 H, m), 1.00 (9 H, s), 0.201 (3 H, s), 0.197 (3 H, s).

B. 3-tert-Butyldimethylsilyloxy-2,5-difluorobenzaldehyde

A 1.0 M solution of sec-BuLi (21.5 ml, 21.5 mmol) was added dropwise to a stirred solution of O-tert-butyldimethylsilyl-2,5-difluorophenol (5.0 g, 20 mmol) in THF (20 mL) at −78° C. After 0.5 hr DMF (1.9 ml, 24.6 mmol) was added dropwise while the temperature was kept below −70° C. After 30 min, the mixture was allowed to warm to room temperature over 30 min. To the mixture was added 3N HCl (30 ml) and stirring was continued for 30 min. The mixture was extracted with ether (100 ml) and the extract was washed with water (100 ml), brine (100 ml), dried (sodium sulfate) and evaporated. Column chromatography (silica gel) of the residue eluting with n-hexane gave 3.56 g (64%) of the titled compound as a colorless oil.

$^1$H NMR (CDCl$_3$) δ: 10.31 (1 H, d, J=2.93 Hz), 7.12 (1 H, ddd, J=3.3, 4.4, 7.7 Hz), 6.89 (1 H, ddd, J=3.3, 7.0, 9.2 Hz), 1.02 (9 H, s), 0.245 (3 H, s), 0.240 (3 H, s).

C. 2,5-Difluoro-3-methoxybezaldehyde

Potassium fluoride (7.79 g, 134 mmol) and iodomethane (4.98 ml, 80 mmol) were added to a stirred solution of 3-tert-butyldimethylsilyloxy-2,5-difluorobenzaldehyde (19.45 g, 67 mmol) in DMF (100 ml) at room temperature. After 5 hr, the mixture was poured into water (100 ml) and extracted with ethyl acetate (200 ml). The extract was washed with water (100 ml), brine (100 ml), dried (magnesium sulfate) and evaporated. The residue was purified by column chromatography (silica gel) eluting with ethyl acetate/n-hexane (1/10) to give 8.58 g (74%) of the titled compound as a white solid.

$^1$H NMR (CDCl$_3$) δ: 10.35 (1 H, d, J=2.93 Hz), 7.08 (1 H, ddd, J=2.9, 4.0, 7.3 Hz), 6.94 (1 H, ddd, J=2.9, 6.6, 9.5 Hz), 3.94 (3 H, s).

D. 2,5-Difluoro-3-methoxybenzyl alcohol

Sodium borohydride (2.83 g, 74.7 mmol) was added to a stirred solution of 2,5-difluoro-3-methoxybenzaldehyde (8.57 g, 49.8 mmol) in ethanol (100 ml) at room temperature. After 30 min, the mixture was concentrated, the residue was diluted with ether (300 ml) and successively washed with water (200 ml), 10% citric acid (200 ml), water (200 ml), brine (200 ml), and dried over magnesiun sulfate. Removal of solvent gave 8.26 g (95%) of the titled compound as a white solid.

$^1$H NMR (CDCl$_3$) δ: 6.80–6.69 (2 H, m), 4.74 (2 H, s), 3.86 (3 H, s), 2.14 (1 H, br s).

E. 2,5-Difluoro-3-methoxyphenylacetonitrile

To a stirred solution of 2,5-difluoro-3-methoxybenzyl alcohol (8.26 g, 47.4 mmol) in dichloromethane (100 ml) was added p-toluenesulfonyl chloride (9.95 g, 52.2 mmol) and triethylamine (7.30 ml, 52.2 mmol) at room temperature. After 3.5 hr, the mixture was poured into water (200 ml) and extracted with ether (200 ml). The extract was washed with brine (200 ml), dried (magnesium sulfate) and evaporated. To the residue was added DMSO (200 ml) and sodium cyanide (3.48 g, 71 mmol). The resulting mixture was stirred for 2 hr and then poured into water (200 ml) and extracted with ether (300 ml). The extract was washed with water (100 ml), brine (100 ml) and dried over magnesium sulfate. Removal of solvent gave 5.91 g (63%) of the titled compound as a red oil.

$^1$H NMR (CDCl$_3$) δ: 6.80–6.65 (2 H, m), 3.89 (3 H, s), 3.76 (2 H, d, J=0.74 Hz).

F. Methyl 2,5-difluoro-3-methoxyphenylacetate

To a stirred solution of 2,5-difluoro-3-methoxyphenylacetonitrile (5.92 g, 30 mmol) in ethylene glycol (150 ml) was added potassium hydroxide (85%; 3.0 g, 45 mmol). The mixture was heated at 120° C. for 1 hr and then the mixture was poured into water (100 ml) and washed with ether (100 ml). The aqueous layer was acidified with 6N HCl (10 ml) and extracted with ether (200 ml). The extract was washed with water (50 ml), brine (50 ml), dried (magnesium sulfate) and evaporated. The residual solid was dissolved in methanol (200 ml) and to the solution was added conc. sulfuric acid (2 ml). The resulting mixture was heated at reflux for 1 hr, cooled and concentrated in vacuo. The residue was dissolved in ether (100 ml), washed with water (100 ml), saturated aqueous sodium hydrogen carbonate (100 ml), brine (100 ml) and dried over magnesium sulfate. Removal of solvent gave 3.80 g (59%) of the titled compound as a yellow oil.

$^1$H NMR (CDCl$_3$) δ: 6.70–6.50 (2 H, m), 3.87 (3 H, s), 3.72 (3 H, s), 3.65 (2 H, d, J=1.84 Hz).

G. Methyl 4-(2,5-difluoro-3-methoxyphenyl)-3,4,5,6-tetrahydropyran-4-carboxylate The titled compound was prepared according to the procedure described in Example 2F except that methyl 2,5-difluoro-3-methoxyphenylacetate was used in place of ethyl 3-benzyloxy-5-fluorophenylacetate.

$^1$H NMR (CDCl$_3$) δ: 6.71–6.59 (2 H, m), 3.93–3.73 (4 H, m), 3.86 (3 H, s), 3.75 (3 H, s), 2.45–2.32 (2 H, m), 2.14–1.96 (2 H, m).

H. Methyl 4-(2,5-difluoro-3-hydroxyphenyl)-3,4,5,6-tetrahydropyran-4-carboxylate The titled compound was prepared according to the procedure described in Example 14C except that methyl 4-(2,5-difluoro-3-methoxyphenyl)-3,4,5,6-tetrahydro-2H-pyran-4-carboxylate was used in place of methyl 1-(3-fluoro-5-hydroxy)cyclopent-3-ene-1-carboxylate.

$^1$H NMR (CDCl$_3$) δ: 6.80–6.50 (2 H, m), 3.96–3.68 (7 H, m), 2.49–2.32 (2 H, m), 2.16–1.95 (2 H, m).

I. Melhyl 4-[2,5-difluoro-3-[4-(2-methylimidazol-1-yl)benzyloxy]phenyl]-3,4,5,6-tetrahydro-2H-pyran-4-carboxylate (Claimed Compound)

Methyl 4-(2,5-difluoro-3-hydroxyphenyl)-3,4,5,6-tetrahydropyran-4-carboxylate was reacted with 4-(2-methylimidazol-1-yl)benzyl chloride hydrochloride according to the procedure described in Example 2H to give the titled compound in 49% yield as a yellow oil.

$^1$H NMR (CDCl$_3$) δ: 7.57 (2 H, d, J=8.4 Hz), 7.34 (2 H, d, J=8.4 Hz), 7.05 (1 H, d, J=1.5 Hz), 7.01 (1 H, d, J=1.5 Hz), 6.90–6.45 (2 H, m), 5.13 (2 H, s), 3.95–3.62 (7 H, m), 2.50–2.30 (5 H, m), 2.16–1.94 (2 H, m).

J. 4-[2,5-Difluoro-3-[4-(2-methylimidazol-1-yl)benzyloxy]phenyl]-3,4,5,6-tetrahydro-2H-pyran-4-carboxamide The titled compound was prepared according to the procedures described in Example 4 and Example 5 except that methyl 4-[2,5-difluoro-3-[4-(2-methylimidazol-1-yl)benzyloxy]phenyl]-3,4,5,6-tetrahydro-2H-pyran-4-carboxylate was used in place of ethyl 4-[5-fluoro-3-[4-(2-methylimidazol-1-yl)benzyloxy]phenyl]-3,4,5,6-tetrahydro-2H-pyran-4-carboxylate.

$^1$H NMR (CDCl$_3$) δ: 7.56 (2 H, d, J=8.43 Hz), 7.34 (2 H, d, J=8.4 Hz), 7.04 (1 H, d, J=1.1 Hz), 7.01 (1 H, d, J=1.5 Hz), 6.82–6.69 (2 H, m), 5.40 (2 H, br s), 5.15 (2 H, s), 4.00–3.70 (4 H, m), 2.50–2.30 (5 H, m), 2.22–2.02 (2 H, m).

Example 24

4-[3-[4-(2-Methylimidazol-1-yl)phenylsulfonyl]phenyl]-3,4,5,6-tetrahydro-2H-pyran-4-carboxamide A mixture of 4-[3-[4-(2-methylimidazol-1-yl)phenylthio]phenyl]-3,4,5,6-tetrahydro-2H-pyran-4-carboxamide (example 8, 1.62 g, 4.00 mmol) and hydrogen peroxide (30% in water, 5.0 ml) in acetic acid (12 ml) was stirred at room temperature for 12 h, then heated at reflux temperature for 2 h. The reaction mixture was then poured into saturated aqueous NaHCO$_3$ (50 ml) and extracted with ethyl acetate (300 ml×2). The combined organic extracts were washed with brine (100 ml), dried (MgSO$_4$) and concentrated in vacuo to afford 1.68 g (quant.) of the titled compound as pale yellow solid.

$^1$H-NMR (CDCl$_3$) δ: 8.10–8.01 (3 H, m), 7.88 (1 H, d, J=7.7 Hz), 7.68 (1 H,d, J=7.0 Hz), 7.57 (1 H, dd, J=7.0, 7.0 Hz), 7.47 (2 H, d, J=8.8 Hz), 7.05 (1 H, d, J=1.5 Hz), 7.01 (1 H, d, J=1.5 Hz), 5.42 (2 H, br.s), 3.91–3.70 (4 H, m), 2.39 (3 H, s), 2.48–2.38 (2 H, m), 2.12–1.99 (2 H, m).

Example 25

4-Cyano-4-[5-fluoro-3-[4-(2-methylimidazol-1-yl)phenylthio]phenyl]-3,4,5,6-tetrahydro-2H-pyran A. 4-Cyano-4-(3,5-difluorophenyl)-3,4,5,6-tetrahydro-2H-pyran To a solution of 3,5-difluorophenylacetonitrile (24.2 g, 0.158 mol) in DMSO (240 ml) was added sodium hydride (60% w/w dispersion in mineral oil, 13.3 g, 0.332 mol) portionwise over 10 min. The reaction mixture was stirred for 40 min at room temperature and then bis-(2-chloroethyl) ether (24.9 g, 0.174 mol) was added slowly and stirring continued for an additional 1 h. The reaction mixture was poured into water (500 ml) and the mixture was extracted with an ethyl acetate-toluene mixture (2:1 v/v, 400 ml×3). The combined extracts were washed with 2 N aqueous HCl (300 ml), water (300 ml) and brine (300 ml), dried (MgSO$_4$) and concentrated to 100 ml. The precipitated solids were collected and washed with cold Et$_2$O (50 ml) to afford 26.3 g (71%) of the titled compound as off white solids.

$^1$H-NMR (CDCl$_3$) δ: 7.15–7.00 (2 H, m), 6.89–6.78 (1 H, m), 4.20–4.05 (2 H, m), 3.98–3.80 (2 H, m), 2.20–1.96 (4 H, m)

B. 4-Cyano-4-(5-fluoro-3-methylthiophenyl)-3,4,5,6-tetrahydro-2H-pyran

Methanethiol was bubbled into a stirred suspension of sodium hydride (65% w/w dispersion in mineral oil, 273 mg, 7.4 mmol) in DMF (10 ml) until a clear solution was obtained. 4-Cyano-4-(3,5-difluorophenyl)-3,4,5,6-tetrahydro-2H-pyran (1.65 g, 7.4 mmol) was added and the resulting mixture was heated at 100° C. for 22 h, cooled and poured into water (100 ml). The mixture was extracted with Et$_2$O (100 ml) and extract washed with water (100 ml), brine (100 ml) and dried (MgSO$_4$). Removal of solvent gave 1.87 g (quant.) of the titled compound as a tan oil.

$^1$H-NMR (CDCl$_3$) δ: 7.20–7.12 (1 H, m), 6.96–6.85 (2 H, m), 4.16–4.04 (2 H, m), 3.79–3.81 (2 H, m), 2.51 (3 H, s), 2.20–1.98 (4 H, m).

C. 4-Cyano-4-(5-fluoro-3-methylsulfinylphenyl)-3,4,5,6-tetrahydro-2H-pyran

The titled compound was prepared according to the procedure described in Example 8D except that 4-cyano-4-(5-fluoro-3-methylthiophenyl)-3,4,5,6-tetrahydro-2H-pyran was used in place of 4-cyano-4-(3-methylthiophenyl)-3,4,5,6-tetrahydro-2H-pyran.

$^1$H-NMR (CDCl$_3$) δ: 7.60–7.54 (1 H, m), 7.41–7.30 (2 H, m), 4.20–4.15 (2 H, m), 3.98–3.81 (2 H, m), 2.78 (3 H, s), 2.25–2.01 (4 H, m).

D. 4-Cyano-4-(5-fluoro-3-mercaptophenyl)-3,4,5,6-tetrahydro-2H-pyran

The titled compound was prepared according to the procedure described in Example 8E except that 4-cyano-4-(5-fluoro-3-methylsulfinylphenyl)-3,4,5,6-tetrahydro-2H-pyran was used in place of 4-cyano-4-(3-methylsulfinylphenyl)-3,4,5,6-tetrahydro-2H-pyran.

$^1$H-NMR (CDCl$_3$) δ: 7.46–6.89 (3 H, m), 4.18–4.00 (2 H, m), 3.96–3.78 (2 H, m), 2.20–1.92 (4 H, m).

E. 4-Cyano-4-[5-fluoro-3-[4-(2-methylimidazol-1-yl)phenylthio]phenyl]-3,4,5,6-tetrahydro-2H-pyran The titled compound was prepared according to the procedure described in Example 8F except that 4-cyano-4-(5-fluoro-3-mercaptophenyl)-3,4,5,6-tetrahydro-2 H-pyran was used in place of 4-cyano-4-(3-mercaptophenyl)-3,4,5, 6-tetrahydro-2H-pyran.

$^1$H-NMR (CDCl$_3$) δ: 7.75–6.89 (9 H, m), 4.15–4.04 (2 H, m), 3.96–3.81 (2 H, m), 2.40 (3 H, s), 2.18–1.98 (4 H, m).

Example 26

4-[5-Fluoro-3-[4-(2-methylimidazol-1-yl)phenylthio] phenyl]-3,4,5,6-tetrahydro-2H-pyran-4-carboxamide To a solution of 4-cyano-4-[5-fluoro-3-[4-(2-methylimidazol-1-yl)phenylthio]phenyl]-3,4,5,6-tetrahydro-2H-pyran (Example 25, 1.71 g, 4.36 mmol) in tert-butanol (20 ml) was added powdered potassium hydroxide (85%, 860 mg, 13 mmol). The resulting mixture was heated at reflux temperature for 4 h, cooled and concentrated in vacuo. Water (50 ml) was added and the precipitates were collected by filtration and washed with 50 ml of ethyl acetate. After drying in vacuo, 560 mg (31%) of the titled compound was obtained as a yellow powder.

$^1$H-NMR (CDCl$_3$) δ: 7.50 (4 H, s), 7.32 (2 H, s), 7.21 (1 H, s), 7.20–6.98 (3 H, m), 6.92 (1 H, s), 3.80–3.62 (2 H, m), 3.52–3.26 (2 H, m), 2.47–2.20 (5 H, m), 1.88–1.67 (2 H, m).

Example 27

4-Cyano-4-[5-fluoro-3-[4-(2-methyl-1H-pyrrol-1-yl) phenylthio]phenyl]-3,4,5,6-tetrahydro-2H-pyran A. 4-(2-Methylpyrrol-1-yl)phenyl iodide The titled compound was prepared from 2-methylpyrrole (*J. Org. Chem.* 1956, 21, 918.) in an analogous manner to that of 4-(pyrrol-1-ylmethyl)phenyl iodide (EP 488 602 A1).

$^1$H-NMR (CDCl$_3$) δ: 7.75 (2 H, d, J=8.5 Hz), 7.04 (2 H, d, J=8.5 Hz), 6.72 (1 H, d, J=1.8 Hz), 6.19 (1 H, d, J=1.8 Hz), 6.04 (1 H, s), 2.20 (3 H, s).

B. 4-Cyano-4-[5-fluoro-3-[4-(2-methyl-1H-pyrrol-1-yl) phenyl thio]phenyl]-3,4,5,6-tetrahydro-2H-pyran The titled compound was prepared according to the procedure described in Example 25E except that 4-(2-methylpyrrol-1-yl)phenyl iodide was used in place of 4-(2-methylimidazol-1-yl)phenyl iodide.

$^1$H-NMR (CDCl$_3$) δ: 7.50 (2 H, d, J=8.8 Hz), 7.33 (2 H, d, J=8.8 Hz), 7.05–6.99 (1 H, m), 6.95–6.87 (2 H, m), 6.79–6.77 (1 H, m), 6.23–6.20 (1 H, m), 5.30 (1 H, s), 4.11–4.05 (4 H, m), 3.93–3.82 (4 H, m), 2.25 (3 H, s).

Example 28

4-[5-Floro-3-[4-(2-methyl-1H-pyrrol-1-yl) phenylthio]phenyl]-3,4,5,6-tetrahydro-2H-pyran-4-carboxamide The titled compound was prepared according to the procedure described in Example 26 except that 4-cyano-4-[5-fluoro-3-[4-(2-methyl-1H-pyrrol-1-yl)phenylthio] phenyl]-3,4,5,6-tetrahydro-2H-pyran was used in place of 4-cyano-4-[5-fluoro-3-[4-(2-methylimidazol-1-yl) phenylthio]phenyl]-3,4,5,6-tetrahydro-2H-pyran.

$^1$H-NMR (DMSO-d$_6$) δ: 7.47 (4 H, dd, J=17.7, 8.4 Hz), 7.30 (1 H, s), 7.18–6.96 (4 H, m), 6.88 (1 H, t, J=2.8 Hz), 6.12–6.08 (1 H, m), 5.99 (1 H, s), 3.73–3.68 (2 H, m), 3.48–3.29 (2 H, m), 2.39–2.33 (2 H, m), 2.19 (3 H, s), 1.77–1.72 (2 H, m).

Example 29

(2SR,4RS)-4-Cyano-2-methyl-4-[3-[4-(2-methylimidazol-1-yl)phenylthio]phenyl]-3,4,5,6-tetrahydro-2H-pyran and (2SR,4SR)-4-Cyano-2-methyl-4-[3-[4-(2-methylimidazol-1-yl)phenylthio]phenyl]-3,4,5,6-tetrahydro-2H-pyran A. 1-Iodo-2-(2-iodoethoxy)propane A mixture of 2-[2-(p-toluenesulfonyloxy)ethoxy]propyl p-toluenesulfonate (*J. Chem. Soc., Perkin Trans* 1 1979, 1029.; 5.7 g, 13 mmol) and sodium iodide (12 g, 80 mmol) in acetone (100 ml) was heated at reflux temperature for 24 h. The mixture was cooled, concentrated in vacuo and water (200 ml) added. The mixture was extracted with Et$_2$O (300 ml), washed with brine (200 ml) and dried (MgSO$_4$). Removal of solvent gave 4.3 g (95%) of the titled compound as a yellow oil.

$^1$H-NMR (CDCl$_3$) δ: 3.87–3.42 (3 H, m), 3.32–3.10 (4 H, m), 1.30 (3 H, d, J=5.9 Hz).

B. (2SR,4RS)-4-Cyano-4-(3-iodophenyl)-2-methyl-3,4,5,6-tetrahydro-2H-pyran and (2SR,4SR)-4-Cyano-4-(3-iodophenyl)-2-methyl-3,4,5,6-tetrahydro-2H-pyran.

The titled compounds were prepared according to the procedure described in Example 25A except that 3-iodophenyacetonitrile and 1-iodo-2-(2-iodoethoxy) propane were used in place of 3,5-difluorophenylacetonitrile and bis-(2-chloroethyl)ether. The diastereomers were separated by silica gel column chromatography to afford 1.46 g (38%) of a less polar isomer, (2SR, 4RS)-4-cyano-4-(3-iodophenyl)-2-methyl-3,4,5,6-tetrahydro-2H-pyran; and 1.31 g (34%) of a more polar isomer, (2SR, 4SR)-4-cyano-4-(3-iodophenyl)-2-methyl-3,4,5,6-tetrahydro-2H-pyran.

(2SR, 4RS)-4-Cyano-4-(3-iodophenyl)-2-methyl-3,4,5,6-tetrahydro-2H-pyran:

$^1$H-NMR (CDCl$_3$) δ: 7.80 (1 H, br.s), 7.74–7.64 (1 H, m), 7.52–7.39 (1 H, m), 7.16 (1 H, dd, J=7.9, 7.9 Hz), 4.20–4.08 (1 H, m), 4.03–3.84 (2 H, m), 2.16–1.97 (3 H, m), 1.69 (1 H, dd, J=13.6, 11.0 Hz), 1.28 (3 H, d, J=6.2 Hz).

(2SR, 4SR)-4-Cyano-4-(3-iodophenyl)-2-methyl-3,4,5,6-tetrahydro-2H-pyran:

$^1$H-NMR (CDCl$_3$) δ: 7.90–7.40 (2 H, m), 7.67–7.40 (1 H, m), 7.32–7.12 (1 H, m), 4.06–3.88 (1 H, m), 3.69–3.42 (2 H, m), 2.62–2.30 (3 H, m), 2.23–2.00 (1 H, m), 1.25 (3 H, d, J=6.2 Hz).

C. (2SR,4RS)-4-Cyano-2-methyl-4-(3-triisopropylsilylthiophenyl)-3,4,5,6-tetrahydro-2H-pyran To a stirred solution of triisopropylsilanethiol (*Tetrahedron Lett.* 1994, 35, 3221.; 684 mg, 3.6 mmol) in toluene (5 ml) was added sodium hydride (60% oil dispersion, 144 mg, 3.6 mmol) under a nitrogen atmosphere. After stirring for 15 min, the resulting solution was added to a mixture of (2SR, 4RS)-4-cyano-4-(3-iodophenyl)-2-methyl-3,4,5,6-tetrahydro-2H-pyran (1.07 g, 3.27 mmol) and tetrakis(triphenylphosphine)palladium(0) (114 mg, 0.1 mmol) in toluene (20 ml), and the mixture was heated at 80° C. for 1 h. The resulting mixture was cooled, poured into water (50 ml) and extracted with Et$_2$O (100 ml). The organic extract was washed with water (50 ml), brine (50 ml), dried (MgSO$_4$) and concentrated. Purification by silica gel column chromatography, eluting with ethyl acetate-hexane (1:9), gave 1.23 g (96%) of the titled compound as a red oil.

$^1$H-NMR (CDCl$_3$) δ: 7.80–7.25 (4 H, m), 3.97–3.82 (1 H, m), 3.60–3.40 (2 H, m), 2.56–2.38 (3 H, m), 2.15–2.00 (1 H, m), 1.36–1.00 (24 H, m).

D. (2SR,4SR)-4-Cyano-2-methyl-4-(3-triisopropylsilylthiophenyl)-3,4,5,6-tetrahydro-2H-pyran The titled compounds was prepared according to the procedure described above except that (2SR, 4SR)-4-cyano-4-(3-iodophenyl)-2-methyl-3,4,5,6-tetrahydro-2H-pyran was used in place of (2SR, 4RS)-4-cyano-4-(3-iodophenyl)-2-methyl-3,4,5,6-tetrahydro-2H-pyran.

$^1$H-NMR (CDCl$_3$) δ: 7.80–7.20 (4 H, m), 4.19–3.85 (3 H, m), 2.12–1.95 (3 H, m), 1.77–1.60 (1 H, m), 1.37–1.00 (24 H, m).

E. (2SR, 4RS)-4-Cyano-2-methyl-4-[3-[4-(2-methylimidazol-1-yl)phenylthio]phenyl]-3,4,5,6-tetrahydro-2H-pyran (Claimed Compound)

To a stirred solution of 4-(2-methylimidazol-1-yl)phenyl iodide (1.21 g, 3.1 mmol) and (2SR, 4RS)-4-cyano-2- methyl-4-(3-triisopropylsilylthiophenyl)-3,4,5,6-tetrahydro-2H-pyran (795 mg, 2.8 mmol) in ethanol (20 ml) was added tetrakis(triphenylphosphine)palladium(0) (215 mg, 0.2 mmol) and potassium tert-butoxide (383 mg, 3.4 mmol) under a nitrogen atmosphere. The resulting mixture was heated at reflux temperature for 15.5 h, then cooled and concentrated in vacuo. The residue was diluted in ethyl acetate (100 ml), and washed with water (2×100 ml), brine (100 ml) and dried (MgSO$_4$) and concentrated. Purification by silica-gel column chromatography, eluting with dichloromethane-methanol (25:1), gave 1.01 g (93%) of the titled compound as a yellow gum.

$^1$H-NMR (CDCl$_3$) δ: 7.75–7.20 (8 H, m), 7.03 (1 H, d, J=1.5 Hz), 7.00 (1 H, d, J=1.1 Hz), 3.97–3.84 (1 H, m), 3,60–3.40 (2 H, m), 2.52–2.30 (6 H, m), 2.08 (1 H, dd, J=14.2, 10.6 Hz), 1.22 (3 H, d, J=6.2 Hz).

F. (2SR, 4SR)-4-Cyano-2-methyl-4-[3-[4-(2-methylimidazol-1-yl)phenylthio]phenyl]-3,4,5,6-tetrahydro-2H-pyran (Claimed Compound)

The titled compound was prepared according to the procedure described above except that (2SR, 4SR)-4-cyano-2-methyl-4-(3-triisopropylsilylthiophenyl)-3,4,5,6-tetrahydro-2H-pyran was used in place of (2SR, 4RS)-4-cyano-2-methyl-4-(3-triisopropylsilylthiophenyl)-3,4,5,6-tetrahydro-2H -pyran.

$^1$H-NMR (CDCl$_3$) δ: 7.74–7.18 (8 H, m), 7.03 (1 H, d, J=1.5 Hz), 7.00 (1 H, d, J=1.5 Hz), 4.20–3.85 (3 H, m), 2.37 (3 H, s), 2.15–1.98 (3 H, m), 1.82–1.64 (1 H, m), 1.27 (3 H, d, J=6.2 Hz).

Example 30

(2SR, 4RS)-2-Methyl-4-[3-[4-(2-methylimidazol-1-yl)phenylthio]phenyl]-3,4,5,6-tetrahydro-2H-pyran-4-carboxamide The titled compound was prepared according to the procedure described in Example 26 except that (2SR, 4RS)-4-cyano-2-methyl-4-[3-[4-(2-methylimidazol-1-yl)phenylthio]phenyl]-3,4,5,6-tetrahydro-2H-pyran was used in place of 4-cyano-4-[5-fluoro-3-[4-(2-methylimidazol-1-yl)phenylthio]phenyl]-3,4,5,6-tetrahydro-2H-pyran.

$^1$H-NMR (CDCl$_3$) δ: 7.50–7.20 (8 H, m), 7.04 (1 H, d, J=1.1 Hz), 6.99 (1 H, d, J=1.5 Hz), 5.18 (2 H, br.s), 3.98–3.84 (1 H, m), 3.55–3.30 (3 H, m), 2.40–2.18 (5 H, m), 1.99 (1 H, dd, J=13.9, 11.4 Hz), 1.18 (3 H, d, J=5.9 Hz).

Example 31

(2SR, 4SR)-2-Methyl-4-[3-[4-(2-methylimidazol-1-yl)phenylthio]phenyl]-3,4,5,6-tetrahydro-2H-pyran-4-carboxamide The titled compound was prepared according to the procedure described in Example 26 except that (2SR, 4SR)-4-cyano-2-methyl-4-[3-[4-(2-methylimidazol-1-yl)phenylthio]phenyl]-3,4,5,6-tetrahydro-2H-pyran was used in place of 4-cyano-4-[5-fluoro-3-[4-(2-methylimidazol-1-yl)phenylthio]phenyl]-3,4,5,6-tetrahydro-2H-pyran.

$^1$H-NMR (CDCl$_3$) δ: 7.53–7.18 (8 H, m), 7.02 (1 H, d, J=1.5 Hz), 6.99 (1 H, d, J=1.1 Hz), 5.37 (2 H, br.s), 4.07–3.95 (1 H, m), 3.87–3.70 (3 H, m), 2.48–2.25 (5 H, m), 1.92 (1 H, ddd, J=12.8, 12.8, 4.8 Hz), 1.24 (3 H, d, J=6.2 Hz).

Example 32

Chiral separation of (2SR, 4RS)-2-methyl-4-[3-[4-(2-methylimidazol-1-yl)phenylthio]phenyl]-3,4,5,6-tetrahydro-2H-pyran-4-carboxamide (example 30)

(2SR, 4RS)-2-methyl-4-[3-[4-(2-methylimidazol-1-yl)phenylthio]phenyl]-3,4,5,6-tetrahydro-2H-pyran-4-carboxamide (example 30, 100 mg) was separated on chiral column chromatography (column: Daicel Chemical Industries LTD; CHIRALPAK AS 2×25 cm, eluent: hexane/ethanol (v/v, 8/2), flow late: 6 ml/min., temperature: 40° C.) to afford 38 mg of the (+)-enantiomer (1st fraction, (+)[α]$_D$=+21°, (C0.1, methanol)) and 44 mg of the (−)-enantiomer (2nd fraction).

Example 33

4-Cyano-4-[3-[4-(1,2,4-triazol-4-yl)phenyl]thiophenyl]-3,4,5,6-tetrahydro-2H-pyran A. 4-Cyano-4-(3-iodophenyl)-3,4,5,6-tetrahydro-2H-pyran A mixture of 3-iodophenylacetonitrile (2.43 g, 10 mmol), bis-(2-chloroethyl)ether (1.57 g, 11 mmol), hexadecyltributylphosphonium bromide (250 mg, 0.5 mmol) and 50% aqueous sodium hydroxide (20 ml) was stirred vigorously for 1 h at room temperature. The mixture was neutralized with 6 N aqueous HCl, transferred to a separatory funnel and extracted with ethyl acetate (50 ml×3). The combined extracts were washed with 2 N aqueous HCl (50 ml), water (50 ml) and brine (50 ml), dried (MgSO$_4$) and concentrated in vacuo. The residual crude solids were collected and washed with cold Et$_2$O (30 ml) to afford 2.38 g (76%) of the titled compound as white solids.

$^1$H-NMR (CDCl$_3$) δ: 7.83–7.80 (1 H, m), 7.73–7.67 (1 H, m), 7.50–7.44 (1 H, m), 7.16 (1 H, dd, J=8.1, 7.7 Hz), 4.14–4.02 (2 H, m), 3.98–3.81 (2 H, m), 2.20–1.99 (2 H, m)

B. 4-Cyano-4-(3-triisopropylsilylthiophenyl)-3,4,5,6-tetrahydro-2H-pyran

The titled compound was prepared according to the procedure described in example 29C for the preparation of (2SR,4RS)-4-cyano-2-methyl-4-(3-triisopropylsilylthiophenyl)-3,4,5,6-tetrahydro-2H-pyran using 4-cyano-4-(3-iodophenyl)-3,4,5,6-tetrahydro-2H-pyran in place of (2SR,4RS)-4-cyano-4-(3-iodophenyl)-2-methyl-3,4,5,6-tetrahydro-2H-pyran.

$^1$H-NMR (CDCl$_3$) δ: 7.62 (1 H, t, J=1.5 Hz), 7.48 (1 H, dt, J=7.0, 1.5 Hz), 7.34 (1 H, dt, J=7.0, 1.5 Hz), 7.28 (1 H, t, J=7.0 Hz), 4.13–4.02 (2 H, m), 3.96–3.83 (2 H, m), 2.18–1.97 (4 H, m), 1.33–1.16 (3 H, m), 1.07 (18 H, d, J=6.6 Hz)

C. 4-Cyano-4-[3-[4-(1,2,4-triazol-4-yl)pheny]thiophenyl]-3,4,5,6-tetrahydro-2H-pyran The titled compound was prepared according to the procedure described in example 29E for the preparation of (2SR,4RS)-4-cyano-2-methyl-4-[3-[4-(2-methylimidazol-1-yl)phenylthio]phenyl]-3,4,5,6-tetrahydro-2H-pyran using 4-(triazol-4-yl)phenyl iodide and 4-cyano-4-(3-triisopropylsilylthiophenyl)-3,4,5,6-tetrahydro-2H-pyran in place of 4-(2-methylimidazol-1-yl)phenyl iodide and (2SR, 4RS)-4-cyano-2-methyl-4-(3-triisopropylsilylthiophenyl)-3,4,5,6-tetrahydro-2H-pyran, respectively. MS(EI): m/z 362 (M$^+$)

The preparation of the requisite 4-(triazol-4-yl)phenyl iodide is outlined below.

Dimethylformazine dihydrochloride (*J. Chem. Soc.* (*C*) 1967, 1664.; 5.38 g, 25 mmol), p-iodoaniline (5.48 g, 25 mmol), and p-toluenesulfonic acid (0.2 g, 1.1 mmol) in toluene (50 ml) were heated at reflux for 3.5 h. Volatiles were removed under reduced pressure and the residue was purified by column chromatography (SiO$_2$, 300 g; 0 to 4% ethanol in dichloromethane) and recrystallization from a mixture of ethanol (10 ml) and dichloromethane (50 ml) to afford 2.63 g (39%) of the requisite compound as needles.

$^1$H-NMR (CDCl$_3$) δ: 8.45 (2 H, s), 7.89 (2 H, d, J=8.8 Hz), 7.16 (2 H, d, J=8.8 Hz).

Example 34

4-[3-[4-(1,2,4-Triazol-4-yl)phenyl]thiophenyl]-3,4,5,6-tetrahydro-2H-pyran-4-carboxamide The titled compound was prepared according to the procedure described in Example 26 except that 4-cyano-4-

[3-[4-(1,2,4-triazol-4-yl)phenyl]thiophenyl]-3,4,5,6-tetrahydro-2H-pyran was used in place of 4-cyano-4-[5-fluoro-3-[4-(2-methylimidazol-1-yl)phenylthio]phenyl]-3,4,5,6-tetrahydro-2H-pyran.

$^1$H-NMR (DMSO-d$_6$) δ: 9.12 (2 H, s), 7.71 (2 H, d, J=8.8 Hz), 7.48–7.36 (5 H, m), 7.28 (1 H, br.s), 7.26–7.21 (1 H, m), 7.08 (1 H, br.s), 3.78–3.68 (2 H, m), 3.51–3.40 (2 H, m), 2.47–2.37 (2 H, m), 1.86–1.73 (2 H, m)

Example 35

4-Cyano-4-[3-[4-(3,5-dimethylpyrazol-1-yl)phenylthio]phenyl]-3,4,5,6-tetrahydro-2H-pyran A. 4-(3,5-Dimethylpyrazol-1-yl)phenyl iodide The titled compound was prepared according to the procedure described in Example 8A except that 3,5-dimethylpyrazole was used instead of 2-methylimidazole.

$^1$H-NMR (CDCl$_3$) δ: 7.76 (2 H, dd, J=6.6, 2.2 Hz), 7.19 (2 H, dd, J=6.6, 2.2 Hz), 6.00 (1 H, s), 2.30 (3 H, d, J=0.7 Hz), 2.28 (3 H, s).

B. 4-Cyano-4-[3-[4-(3,5-dimethylpyrazol-1-yl)phenylthio]phenyl]-3,4,5,6-tetrahydro-2H-pyran The titled compound was prepared according to the procedure described in example 29E for the preparation of (2SR,4RS)-4-cyano-2-methyl-4-[3-[4-(2-methylimidazol-1-yl) phenylthio]phenyl]-3,4,5,6-tetrahydro-2H-pyran using 4-(3,5-dimethylpyrazol-1-yl)phenyl iodide and 4-cyano-4-(3-triisopropylsilylthiophenyl)-3,4,5,6-tetrahydro-2H-pyran in place of 4-(2-methylimidazol-1-yl)phenyl iodide and (2SR,4RS)-4-cyano-2-methyl-4-(3-triisopropylsilylthiophenyl)-3,4,5,6-tetrahydro-2H-pyran, respectively.

$^1$H-NMR (CDCl$_3$) δ: 7.71–7.23 (8 H, m), 6.01(1 H, s), 4.11–4.05 (2 H, m), 3.94–3.83 (2 H, m), 2.33 (3 H, s), 2.29 (3 H, s), 2.14–2.00 (4 H, m).

Example 36

4-[3-[4-[3,5-Dimethylpyrazol-1-yl)phenylthio]phenyl]-3,4,5,6-tetrahydro-2H-pyran-4-carboxamide The titled compound was prepared according to the procedure described in Example 26 except that 4-cyano-4-[3-[4-(3,5-dimethylpyrazol-1-yl)phenylthio]phenyl]-3,4,5,6-tetrahydro-2H-pyran was used in place of 4-cyano-4-[5-fluoro-3-[4-(2-methylimidazol-1-yl)phenylthio]phenyl]-3,4,5,6-tetrahydro-2H-pyran.

$^1$H-NMR (DMSO-d$_6$) δ: 7.51–7.21 (9 H, m), 7.07 (1 H, s), 6.07 (1 H, s), 3.78–3.67 (2 H, m), 3.52–3.38 (2 H, m), 2.42–2.37 (2 H, m ), 2.30 (3 H, s), 2.16 (3 H, s), 1.83–1.71 (2 H, m).

Example 37

4-Cyano-4-[3-[4-(2-methylimidazol-1-yl]phenoxy]phenyl-3,4,5,6-tetrahydro-2H-pyran A. 4-Cyano-4-(3-methoxyphenyl)-3,4,5,6-tetrahydro-2H-pyran The titled compound was prepared according to the procedure described in Example 25A except that 3-methoxyphenylaceonitrile was used instead of 3-iodophenylacetonitrile (80%).

$^1$H-NMR (CDCl$_3$) δ: 7.34 (1 H, t, J=8 Hz), 7.09–7.02 (2 H, m), 6.88 (1 H, ddd, J=8, 3, 1.5 Hz), 4.11–4.06 (2 H, m), 3.95–3.84 (2 H, m), 3.84 (3 H, s), 2.15–2.04 (4 H, m)

B. 4-Cyano-4-(3-hydroxyphenyl)-3,4,5,6-tetrahydro-2H-pyran

To a dichloromethane (80 ml) solution of 4-cyano-4-(3-methoxyphenyl)-3,4,5,6-tetrahydro-2H-pyran (2.32 g, 10.35 mmol) cooled to 0° C. was added boron tribromide (3.15 ml, 33.3 mmol) dropwise over 10 min. The ice-bath was removed and the reaction mixture stirred at ambient temperature for 19 h, and then at reflux for 4 h. The reaction mixture was cooled and poured into water (150 ml). The organic layer was separated and the aqueous layer was extracted with ethyl acetate (50 ml×3). The combined organic extracts were washed with brine (50 ml), dried (MgSO$_4$) and concentrated in vacuo. The crude product was crystallized from isopropyl ether to afford titled compound as off-white solids (1.43 g, 66%).

$^1$H-NMR (CDCl$_3$) δ: 7.29 (1 H, t, J=8 Hz), 7.04 (1 H, dd, J=8, 2 Hz), 6.98 (1 H, dd, J=4, 2 Hz), 6.83 (1 H, dd, J=8, 4 Hz), 5.14 (1 H, br.s), 4.09 (2 H, dd, J=10, 2 Hz), 3.90 (2 H, dt, J=12, 2 Hz), 2.14–2.01 (4 H, m).

C. 4-Cyano-4-[3-[4-(2-methylimidazol-1-yl)phenoxy]phenyl]-3,4,5,6-tetrahydro-2H-pyran A mixture of 4-(2-methylimidazol-1-yl)phenyl iodide (1.28 g, 4.5 mmol), 4-cyano-4-(3-hydroxyphenyl)-3,4,5,6-tetrahydro-2H-pyran (1.20 g, 5.9 mmol) and K$_2$CO$_3$ (4.15 g, 30 mmol) in pyridine (50 ml) was heated at 130° C., cupric oxide (636 mg, 8.0 mmol) added and the reaction mixture was heated under reflux for 2 days. The reaction mixture was cooled and filtered through a celite pad and the solids were washed with ethyl acetate (100 ml). The filtrate was concentrated in vacuo, and the resulting residue was diluted with water (100 ml) and extracted with ethyl acetate (50 ml×3). The combined organic extracts were washed with 1 N aqueous NaOH (100 ml), water (100 ml) and brine (100 ml), dried (Na$_2$SO$_4$) and concentrated in vacuo. The residue was purified by column chromatography {LiChroprep NH$_2$ (Merck), 100 g; eluted with hexane/ethyl acetate (1/1)} to afford 620 mg (38%) of the titled compound as a yellow oil.

$^1$H-NMR (CDCl$_3$) δ: 7.44 (1 H, dd, J=8.1, 7.7 Hz), 7.33–7.21 (4 H, m), 7.12–6.98 (5 H, m), 4.15–4.04 (2 H, m), 3.99–3.82 (2 H, m), 2.37 (3 H, s), 2.22–2.00 (4 H, m).

Example 38

4-[3-[4-(2-Methylimidazol-1-yl)phenoxy]phenyl]-3,4,5,6-tetrahydro-2H-pyran-4-carboxamide The titled compound was prepared according to the procedure described in Example 26 except that 4-cyano-4-[3-[4-(2-methylimidazol-1-yl)phenoxy]phenyl]-3,4,5,6-tetrahydro-2H-pyran was used in place of 4-cyano-4-[5-fluoro-3-[4-(2-methylimidazol-1-yl)phenylthio]phenyl]-3,4,5,6-tetrahydro-2H-pyran.

$^1$H-NMR (CDCl$_3$) δ: 7.40 (1 H, dd, J=8.1, 7.7 Hz), 7.29–7.13 (4 H, m), 7.09–6.95 (5 H, m), 5.32 (2 H, br.s), 3.89–3.70 (4 H, m), 2.43–2.32 (2 H, m), 2.40 (3 H, s), 2.16–2.02 (2 H, m).

Example 39

4-Methoxyiminomethyl-4-[3-[4-(2-methylimidazol-1-yl)phenylthio]phenyl]-3,4,5,6-tetrahydro-2H-pyran A. 4-(3-Iodophenyl)-3,4,5,6-tetrahydro-2H-pyran-4-carbadehyde To a stirred solution of 4-cyano-4-(3-iodophenyl)-3,4,5,6-tetrahydro-2H-pyran (3.3 g, 10.5 mmol) in dry dichloromethane (15 ml) was added dropwise a solution of DIBAL (10.7 ml, 10.5 mmol) at −78° C. under argon atmosphere. After completion of addition, the mixture was stirred for 3 h at the same temperature. To the reaction mixture was carefully added 1 ml of ethanol, then 10 ml of 1 N aqueous HCl was added and the mixture was stirred for 0.5 h. The aqueous mixture was extracted with dichloromethane (20 ml×3) and the combined organic layers were washed with water (50 ml) and brine (50 ml). The extract was dried (MgSO$_4$) and concentrated in vacuo. Chromatographic purification of the residue {SiO$_2$, 150 g; eluted with hexane/ ethyl acetate (5/1)} provided 2.61 g (79%) of desired product as a colorless oil.

¹H-NMR (CDCl₃) δ: 9.40 (1H, s), 7.65 (1 H, ddd, J=7.7, 1.8, 1.1 Hz), 7.62 (1 H, dd, J=1.8, 1.5 Hz), 7.26 (1 H, ddd, J=8.1, 1.5, 1.1 Hz), 7.13 (1 H, dd, J=8.1, 7.7 Hz), 3.95–3.82 (2 H, m), 3.61–3.49 (2 H, m), 2.43–2.28 (2 H, m), 2.12–1.99 (2 H, m).

B. 4-(3-Iodophenyl)-4-methoxyiminonethyl-3,4,5,6-tetrahydro-2H-pyran 4-(3-Iodophenyl)-3,4,5,6-tetrahydro-2H-pyran-4-carbadehyde (1.5 g, 4.7 mmol) and O-methylhydroxylamine hydrochloride (1.0 g, 12 mmol) were dissolved in a mixture of methanol (8 ml) and pyridine (2 ml) and stirred together overnight at ambient temperature. The reaction mixture was concentrated in vacuo and the resultant residue was diluted with 1 N aqueous HCl (50 ml) and extracted with dichloromethane (20 ml×3). The combined organic layers were washed with water (50 ml) and brine (50 ml), dried (MgSO₄) and concentrated in vacuo. The residue was purified by column chromatography {SiO₂, 100 g; eluted with hexane/ethyl acetate (5/1)} to afford 1.35 g (83%) of desired product as a light yellow oil.

¹H-NMR (CDCl₃) δ: 7.64 (1 H, dd, J=1.8, 1.8 Hz), 7.59 (1 H, ddd, J=7.7, 1.8, 1.1 Hz), 7.34 (1 H, s), 7.30 (1 H, ddd, J=8.1, 1.8, 1.1 Hz), 7.09 (1 H, dd, J=8.1, 7.7 Hz), 3.88 (3 H, s), 3.87–3.72 (4 H, m), 2.21–2.02 (4 H, m).

C. 4-[3-[4-(2-Methylimidazol-1-yl)phenylthio]phenyl]-4-methoxyiminomethyl-3,4,5,6-tetrahydro-2H-pyran A 30-ml two-necked flask was equipped with a stopper, a nitrogen inlet and a magnetic stirring bar. The flask was charged with sodium cyanoborohydride (13 mg, 0.2 mmol) and flushed with nitrogen (this process was repeated twice). Bis(triethylphosphine)nickel(II)chloride (41 mg, 0.1 mmol), 4-(3-iodophenyl)-4-methoxyiminomethyl-3,4,5,6-tetrahydro-2H-pyran (1.2 g, 2.6 mmol) and thiourea (286 mg, 3.8 mmol) were then added and the flask was flushed with nitrogen three times. N,N-Dimethylformamide (2 ml) was added and the resulting mixture was heated at 60° C. for 4 h. After cooling to room temperature, calcium oxide (210 mg, 3.8 mmol) and DMF (4 ml) were added. The resulting mixture was stirred at room temperature under nitrogen for 1.5 h and then a mixture of 4-(2-methylimidazol-1-yl)phenyl iodide (780 mg, 2.8 mmol), bis(triethylphosphine)nickel(II) chloride (41 mg, 0.1 mmol) and sodium cyanoborohydride (13 mg, 0.2 mmol) was added. The resulting red mixture was heated at 60° C. under nitrogen for 4 h and then cooled to room temperature. The resulting deep red mixture was partitioned between water (50 ml) and dichloromethane (50 ml) and the organic phase was separated. The aqueous phase was extracted with dichloromethane (20 ml×2). The combined extracts were washed with water (50 ml) and brine (50 ml), dried (MgSO₄) and concentrated in vacuo. The residue was purified by silica gel column chromatography {LiChroprep NH₂ (Merck), 50 g; eluted with ethyl acetate} to afford 388 mg (37%) of desired compound as a colorless oil.

¹H-NMR (CDCl₃) δ 7.48–7.16 (9 H, m), 7.02 (1 H, d, J=1.1 Hz), 6.98 (1 H, d, J=1.1 Hz), 3.90–3.69 (4 H, m), 3.85 (3 H, s), 2.36 (3 H, s), 2.22–2.01 (4 H, m).

Example 40

Methyl 4-[3-[4-(2-methylimidazol-1-yl)phenylthio]phenyl]-3,4,5,6-tetrahydro-2H-pyran-4-carboxylate 4-[3-[4-(2-methylimidazol-1-yl)phenylthio]phenyl]-3,4,5,6-tetrahydro-2H-pyran-4-carboxamide (1.0 g, 2.5 mmol) was dissolved in large excess of HCl-methanol (10 ml) and the solution was refluxed overnight. The volatiles were removed under reduced pressure, the residue was partitioned between 0.5 N aqueous NaOH (50 ml) and ethyl acetate (50 ml) and the organic phase was separated. The aqueous phase was extracted with ethyl acetate (20 ml×2). The combined extracts were washed with water (50 ml) and brine (50 ml), dried (MgSO₄) and concentrated in vacuo to give 360 mg (35%) of the titled compound.

¹H-NMR (CDCl₃) δ: 7.47–7.18 (8 H, m), 7.07–6.60 (2 H, m), 4.00–3.87 (2 H, m), 3.68 (3 H, s), 3.60–3.49 (2 H, m), 2.55–2.44 (2 H, m), 2.35 (3 H, s), 2.00–1.83 (2 H, m).

Example 41

4-[3-[4-(2-Methylimidazol-1-yl)phenylthio]phenyl]-3,4,5,6-tetrahydro-2H-pyran-4-carbaldehyde A. 4-[3-[4-(2-Methylimidazol-1-yl)phenylthio]phenyl]-3,4,5,6-tetrahydro-2H-pyran-4-yl]methanol To a stirred solution of methyl 4-[3-[4-(2-methylimidazol-1-yl)phenylthio]phenyl]-3,4,5,6-tetrahydro-2H-pyran-4-carboxylate (359 mg, 0.9 mmol) was added LAH (80 mg, 2.0 mmol) at 0° C. After completion of addition, the mixture was allowed to warm to room temperature. To the reaction mixture was carefully added water (1 ml), and the resulting solids were dissolved in 1 N aqueous HCl and the aqueous solution was basified with 1 N aqueous NaOH. The aqueous mixture was extracted with ethyl acetate (30 ml×3), and the combined extracts were washed with water (50 ml) and brine (50 ml), dried (MgSO₄) and concentrated in vacuo. The residue was purified by column chromatography {LiChroprep NH₂ (Merck), 20 g; eluted with ethyl acetate} to afford 231 mg (69%) of the desired compound as white solids.

¹H-NMR (CDCl₃) δ: 7.45–7.29 (6 H, m), 7.20 (2 H, d, J=8.8 Hz), 7.01 (1 H, d, J=1.5 Hz), 6.98 (1 H, d, J=1.5 Hz), 3.86–3.70 (2 H, m), 3.64 (2 H, s), 3.62–3.48 (2 H, m), 2.35 (3 H, s), 2.18–2.05 (2 H, m), 2.00–1.87 (2 H, m), 1.67 (1 H, br.s).

B. 4-[3-[4-(2-Methylimidazol-1-yl)phenylthio]phenyl]-3,4,5,6-tetrahydro-2H-pyran-4-carbaldehyde A solution of [4-[3-[4-(2-methylimidazol-1-yl)phenylthio]phenyl]-3,4,5,6-tetrahydro-2H-pyran-4-yl]methanol (230 mg, 0.6 mmol) in dichloromethane (5 ml) was added dropwise to the Swern reagent [1.2 mmol, 2 equiv., prepared by adding a solution of DMSO (143 mg) in dichloromethane (5 ml) to a solution of oxalyl chloride (155 mg, 1.2 mmol) in dichloromethane (10 ml) at −78° C. ] under argon at −78° C. The reaction mixture was stirred for 0.5 h at −78° C. and then this was allowed to warm to −20° C. over 2 h. To the reaction mixture was added triethylamine (1 ml) and the resulted solution was stirred for 0.5 h at 0° C. The mixture was partitioned between saturated aqueous NH₄Cl (50 ml) and ethyl acetate (50 ml), the organic phase was separated and the aqueous phase was extracted with ethyl acetate (20 ml×2). The combined organic extracts were washed with water (50 ml) and brine (50 ml), dried (MgSO₄) and concentrated in vacuo. The residual oil was purified by column chromatography {SiO₂, 100 g; eluted with dichloromethane/ethanol (20/1)} to afford 178 mg (77%) of the titled compound as white solids.

¹H-NMR (CDCl₃) δ: 9.43 (1 H, s), 7.46–7.31 (5 H, m), 7.27–7.18 (3 H, m), 7.03 (1 H, d, J=1.5 Hz), 6.99 (1 H, d, J=1.5 Hz), 3.97–3.83 (2 H, m), 3.65–3.51 (2 H, m), 2.45–2.28 (2 H, m), 2.37 (3 H, s), 2.15–1.98 (2 H, m).

Example 42

4-Hydroxyiminomethyl-4-[3-[4-(2-methlimidazol-1-yl)phenylthio]phenyl]-3,4,5,6-tetrahydro-2H-pyran 4-[3-[4-(2-Methylimidazol-1-yl)phenylthio]phenyl]-3,4,5,6-tetrahydro-2H-pyran-4-carbaldehyde (178 mg, 0.47 mmol) and hydroxylamine hydrochloride (210 mg, 3 mmol) were dissolved in a mixture of methanol (4 ml) and pyridine (1 ml) and the reaction mixture was stirred for 5 h at ambient temperature. Volatiles were removed in vacuo and the resultant residue was diluted with 0.1 N aqueous NaOH (20 ml) and extracted with ethyl acetate (30 ml×3). The combined organic layers were washed with water (50 ml) and brine (50 ml), dried (MgSO$_4$) and concentrated in vacuo. The residual solids were recrystallized from ethyl acetate to afford 130 mg (70%) of the titled compound as white solids.

$^1$H-NMR (DMSO-d$_6$) δ: 10.80 (1 H, s), 7.48–7.25 (10 H, m), 6.91 (1 H, s), 3.73–3.51 (4 H, m), 2.28 (3 H, s), 2.22–2.10 (2 H, m), 2.00–1.88 (2 H, m).

Example 43

4-Cyan-4-[5-fluoro-3-[4-(2-methylpyrrol-1-ylmethyl)phenylthio]phenyl]-3,4,5,6-tetrahydro-2H-pyran A. 4-(2-Methylpyrrol-1-ylmethyl)phenyl iodide The titled compound was prepared from 2-methylpyrrole (*J. Org. Chem.* 1956, 21, 918.) in an analogous manner to that of 4-(pyrrol-1-ylmethyl)phenyl iodide (EP 488 602 A1).

$^1$H-NMR (CDCl$_3$) δ: 7.62 (2 H, d, J=8.4 Hz), 6.72 (2 H, d, J=8.4 Hz), 6.61–6.59 (1 H, m), 6.12–6.10 (1 H, m), 5.94–5.92 (1 H, m), 4.96 (2 H, s), 2.11 (3 H, d, J=0.7 Hz).

B. 4-Cyano-4-[5-fluoro-3-[4-(2-methylpyrrol-1-ylmethyl)phenylthio]phenyl]-3,4,5,6-tetrahydro-2H-pyran The titled compound was prepared according to the procedure described in Example 25E except that 4-(2-methylpyrrol-1-ylmethyl)phenyl iodide was used in place of 4-(2-methylimidazol-1-yl)phenyl iodide.

$^1$H-NMR (CDCl$_3$) δ: 7.39 (2 H, d, J=8.1 Hz), 7.14 (1 H, s), 7.00 (2 H, d, J=8.1 Hz), 7.00–6.95 (1 H, m), 6.78 (1 H, d, J=8.8 Hz), 6.64 (1 H, t, J=2.2 Hz), 6.12–6.10 (1 H, m), 5.95 (1 H, br.s), 5.05 (2 H, s), 4.10–4.04 (2 H, m), 3.91–3.81 (2 H, m), 2.14 (3 H, s), 2.05–1.99 (4 H, m).

Example 44

4-[5-Fluoro-3-[4-(2-methylpyrrol-1-ylmethyl) phenylthio]phenyl]-3,4,5,6-tetrahydro-2H-pyran -4-carboxamide The titled compound was prepared according to the procedure described in Example 26 except that 4-cyano-4-[5-fluoro-3-[4-(2-methylpyrrol-1-ylmethyl)phenyl thio] phenyl]-3,4,5,6-tetrahydro-2H-pyran was used in place of 4-cyano-4-[5-fluoro-3-[4-(2-methylimidazol-1-yl) phenylthio]phenyl]-3,4,5,6-tetrahydro-2H-pyran.

$^1$H-NMR (DMSO-d6) δ: 7.40 (2 H, d, J=8.0 Hz), 7.28 (1 H, s), 7.11–7.04 (3 H, m), 7.05 (2 H, d, J=8.0 Hz), 6.81–6.74 (2 H, m), 5.93 (1 H, t, J=2.9 Hz), 5.82–5.79 (1 H, m), 5.11 (2 H, s), 3.72–3.67 (2 H, m), 3.47–3.39 (2 H, m), 2.36–2.30 (2 H, m), 2.05 (3 H, s), 1.79–1.68 (2 H, m).

We claim:

1. A method to produce a compound of the following chemical formula I:

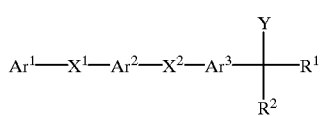

I and the pharmaceutically acceptable salts thereof, wherein

Ar$^1$ is a heterocyclic moiety which is selected from the group consisting of imidazolyl, pyrrolyl, pyrazolyl, 1,2,3-triazolyl, 1,2,4-triazolyl, indolyl, indazolyl and benzimidazolyl, which is bonded to X$^1$ through a ring nitrogen atom, and which may be optionally substituted with one or two substituents selected from halo, hydroxy, cyano, amino, C$_{1-4}$ alkyl, C$_{1-4}$ alkoxy, C$_{1-4}$ alkylthio, C$_{1-4}$ halo-substituted alkyl, C$_{1-4}$ halo-substituted alkoxy, C$_{1-4}$ alkylamino and di(C$_{1-4}$) alkylamino;

X$^1$ is a direct bond or C$_{1-4}$ alkylene;

Ar$^2$ is phenylene optionally substituted with one or two substituents selected from halo, hydroxy, cyano, amino, C$_{1-4}$ alkyl, C$_{1-4}$ alkoxy, C$_{1-4}$ alkylthio, C$_{1-4}$ halo-substituted alkyl and C$_{1-4}$ halo-substituted alkoxy;

X$^2$ is —A—X— or —X—A— wherein A is a direct bond or C$_{1-4}$ alkylene and X is oxy, thio, sulfinyl or sulfonyl;

Ar$^3$ is phenylene, pyridylene, thienylene, furylene, oxazolylene or thiazolylene optionally substituted with one or two substituents selected from halo, hydroxy, cyano, amino, C$_{1-4}$ alkyl, C$_{1-4}$ alkoxy, C$_{1-4}$ alkylthio, C$_{1-4}$ halo-substituted alkyl, C$_{1-4}$ halo-substituted alkoxy, C$_{1-4}$ alkylamino and di(C$_{1-4}$) alkylamino;

R$^1$ and R$^2$ are each C$_{1-4}$ alkyl, or together they form a group of formula —D$^1$—Z—D$^2$— which together with the carbon atom to which it is attached defines a ring having 3 to 8 atoms, wherein D$^1$ and D$^2$ are C$_{1-4}$ alkylene and Z is a direct bond or oxy, thio, sulfinyl, sulfonyl, or vinylene, and D$^1$ and D$^2$ may be substituted by C$_{1-3}$ alkyl; and Y is CONR$^3$R$^4$, CN, C(R$^3$)=N—OR$^4$, COOR$^3$, COR$^3$ or CSNR$^3$R$^4$, wherein R$^3$ and R$^4$ are each H or C$_{1-4}$ alkyl; comprising reacting a compound of the formula (II) with a compound of the formula (III):

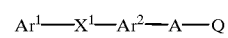

II

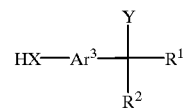

III or, reacting a compound of the formula (IV) with a compound of the formula (V):

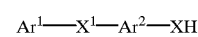

IV

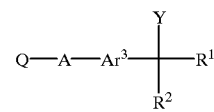

V wherein Ar$^1$, Ar$^2$, Ar$^3$, R$^1$, R$^2$, A, X, X$^1$, and Y are defined as above; and Q is a displaceable group, in a reaction-inert solvent.

2. A process according to claim 1, wherein the solvent is selected from acetone, acetonitrile, dichloromethane, N,N-dimethylacetamide, N,N-dimethylformamide, dimethylsulfoxide, dioxane and tetrahydrofuran; and the reaction is carried out at from room temperature to reflux temperature of the solvent used.

3. A process according to claim 1, wherein the reaction is carried out in the presence of a catalyst selected from tetrakis(triphenylphosphine) palladium, bis(triphenylphosphine)palladium(II) chloride, cuprous oxide, cuprous iodide, cuprous bromide and cuprous chloride.

4. A process according to claim 1, wherein the reaction is carried out in the presence of the base selected from sodium ethoxide, sodium tert-butoxide, potassium tert-butoxide, sodium fluoride, potassium fluoride, cesium fluoride and tetra-butylammonium fluoride.

* * * * *